United States Patent [19]

Acevedo et al.

[11] Patent Number: 5,519,134
[45] Date of Patent: May 21, 1996

[54] PYRROLIDINE-CONTAINING MONOMERS AND OLIGOMERS

[75] Inventors: Oscar L. Acevedo, San Diego; Normand Hebert, San Marcos, both of Calif.

[73] Assignee: Isis Pharmaceuticals, Inc., Carlsbad, Calif.

[21] Appl. No.: 180,134

[22] Filed: Jan. 11, 1994

[51] Int. Cl.$^6$ ...................... C07D 207/08; C07D 207/06; C07D 207/10; C07D 233; C07D 58; C07D 233/60; C07D 239/26

[52] U.S. Cl. .......................... 544/243; 544/35; 544/102; 544/104; 544/242; 544/262; 544/264; 544/267; 544/277; 544/298; 544/309; 544/311; 544/313; 544/314; 544/317; 544/335; 548/314.7; 548/361.1; 548/361.5; 548/362.1; 548/362.5; 548/364.1; 548/412; 548/413; 548/440; 548/441; 548/443; 548/444; 548/446; 548/465; 548/466; 548/467; 548/518; 548/519; 548/523; 548/524; 548/530; 548/531; 548/542; 548/546

[58] Field of Search ................................. 548/412, 413, 548/530, 531, 542, 546, 314.7, 518, 519, 523, 524, 364.1, 465, 466, 467, 361.1, 361.5, 362.1, 362.5, 440, 441, 443, 444, 446; 544/242, 243, 298, 335, 102, 104, 35

[56] References Cited

U.S. PATENT DOCUMENTS

| | | | |
|---|---|---|---|
| 3,687,808 | 8/1972 | Merigan, Jr. et al. | 195/28 |
| 5,210,264 | 5/1993 | Yau | 558/167 |
| 5,218,105 | 6/1993 | Cook et al. | 536/25.31 |

OTHER PUBLICATIONS

CA 106:213757w Pyrrolidine derivatives. p. 644, 1987.
Owens et al., "The Rapid Identification of HIV Protease Inhibitors Through the Synthesis and Screening of Defined Peptides Mixtures," *Biochem. Biophys. Res. Commun.*, 181:402–408, 1991.
Pruzanski et al., "Enzymatic Activity and Immunoreactivity of Extracellular Phospholipase A$_2$ in Inflammatory Synovial Fluids," *Inflammation*, 16:451–457, 1992.
Remuzon et al., "Preparation of (6R)– and (6S)–(1R, 4R)–6–Methyl–2–(p–toluene–Sulfonyl)–5–Phenylmethyl–2,5–Diazabicyclo[2.2.1]Heptanes, Intermediates in a Synthesis of New Quinolones," *Heterocycles*, 34:241–245, 1992.
Remuzon et al., "Synthesis of (1R,4R,7S)– and (1S,4S,7S)–2–(4–Tolylsulfonyl)–5–phenyl–methyl–7–2,5–diazabicyclo[2.2.1]heptanes via Regioselective Opening of 3,4–Epoxy–D–proline with Lithium Dimethyl Cuprate," *Heterocyclic Chem.*, 30:517–523, 1993.
Rosen et al., "Design, Synthesis, and Properties of (4S)–7–(4–Amino–2–substituted–pyrrolidin–1–yl) quinolone–3–carboxylic Acids," *J. Med. Chem.*, 31:1598–1611, 1988.
Scott et al., "Interfacial Catalysis: The Mechanism of Phospholipase A$_2$," *Science*, 250:1541–1546, 1990.

Tanaka et al., "A Novel Type of Phospholipase A$_2$ Inhibitor, Thielocin A1β, and Mechanism of Action," *J. Antibiotics*, 45:1071–1078, 1992.
Vishwanath et al., "Edema–Inducing Activity of Phospholipase A$_2$ Purified from Human Synovial Fluid and Inhibition by Aristolochic Acid," *Inflammation*, 12:549–561, 1988.
Washburn et al., "Suicide–inhibitory Bifunctionally Linked Substrates (SIBLINKS) as Phospholipase A$_2$ Inhibitors," *J. Biol. Chem.*, 266:5042–5048, 1991.
Jordis et al., "Synthesis of (1R,4R)– and (1S,4S)–2,5–Diazabicyclo[2.2.1]heptanes and their N–substituted Derivatives," *Synthesis*, 925–930, 1990.
Kroschwitz, J., ed., "Polynucleotides," *Concise Encyclopedia of Polymer Science and Engineering*, John Wiley & Sons, Inc., 858–859, 1990.
Lombardo et al., "Cobra Venom Phospholipase A$_2$ Inhibition by Manoalide," *J. Biol. Chem.*, 260:7234–7240, 1985.
Marki et al., "Differential inhibition of human secretory and cytosolic phospholipase A$_2$," *Agents Actions*, 38:202–211, 1993.
McKennon et al., "A Convenient Reduction of Amino Acids and Their Derivatives," *J. Org. Chem.*, 58:3568–3571, 1993.
Mellor, D. P., *Chemistry of Chelation and Chelating Agents in International Encyclopedia of Pharmacology and Therapeutics*, Section 70, The Chelation of Heavy Metals, Levine, W. G., Ed., New York: Pergamon Press, 1979.
Miyake et al., "The Novel Natural Product YM–26567–1 [(+)–trans–4–(3–dodecanoyl–2,4, 6–trihydroxyphenyl)–7–hydroxy–2–(4–hydroxyphenyl) chroman]: A Competitive Inhibitor of Group II Phospholipase A$_2$," *J. Pharmacol. Exp. Ther.*, 263:1302–1307, 1992.
Noel et al., "Phospholipase A$_2$. 3. Replacement of Lysine–56 by Neutral Residues Improves Catalytic Potency Significantly, Alters Substrate Specificity, and Clarifies the Mechanism of Interfacial Recognition," *J. Am. Chem. Soc.*, 112:3704–3706, 1990.
Oinuma et al., "Synthesis and Biological Evaluation of Substituted Benzenesulfonamides as Novel Potent Membrane–Bound Phospholipase A$_2$ Inhibitors," *J. Med. Chem.*, 34:2260–2267, 1991.
Franson, et al, "Phospholipid metabolism by phagocytic cells. Phospholipases A$_2$ associated with rabbit polymorphonuclear leukocyte granules", *J. Lipid Res.*, 15:380–388, 1974.
Freeman, J. P., ed., "Reduction of alpha–amino Acids: L–Valinol", *Organic Syntheses*, New York: John Wiley & Sons, Inc., 530–533, 1990.

(List continued on next page.)

*Primary Examiner*—Joseph K. McKane
*Attorney, Agent, or Firm*—Woodcock Washburn Kurtz Mackiewicz & Norris

[57] ABSTRACT

Novel pyrrolidine monomers bearing various functional groups are used to prepare oligomeric structures. The pyrrolidine monomers can be joined via standard phosphate linkages including phosphodiester and phosphorothioate linkages. Useful functional groups include nucleobases as well as polar groups, hydrophobic groups, ionic groups, aromatic groups and/or groups that participate in hydrogen-bonding.

16 Claims, 1 Drawing Sheet

OTHER PUBLICATIONS

Gait, M. J., ed., *Oligonucleotide Synthesis, A Practical Approach*, Oxford: IRL Press, 1984.

Geysen, et al,. "Strategies for epitope analysis using peptide synthesis", *J. Immun. Meth.*, 102:259–274, 1987.

Glaser, et al., "Phospholipase $A_2$ enzymes: regulation and inhibition", *TIPS Review*, 14:92–98, 1993.

Grainger, et al., "An enzyme caught in action: direct imaging of hydrolytic function and domain formation of phospholipase $A_2$ in phosphatidylcholine monolayers", *FEBS Lett.*, 252:73–82, 1989.

Green, et al., *Protective Groups in Organic Synthesis*, 2d Ed., New York: John Wiley & Sons, Inc., 1991.

Houghten, et al., "Generation and use of synthetic peptide combinatorial libraries for basic research and drug discovery", *Nature*, 354:84–86, 1991.

Jaeger, et al., "Pyrrolidinediols. 1–Substituted 3-Hydroxymethyl–4–hydroxypyrrolidines and Derivatives", *J. Organic Chemistry*, 30:740–744, 1965.

Achari et al., "Facing up to Membranes: Structure/Function Relationships in Phospholipases," *Cold Spring Harbor Symp. Quant. Biol.*, 52:441–452, 1987.

Agrawal, S., ed., *Protocols for Oligonucleotides and Analogs*, New Jersey: Humana Press, 1993.

Alul et al., "Oxalyl–CPG: a labile support for synthesis of sensitive oligonucleotide derivatives," *Nucleic Acids Research*, 19:1527–1532, 1991.

Beaucage et al., "Advances in the Synthesis Oligonucleotides by the Phosphoramidite Approach," *Tetrahedron*, 48:2223–2311, 1992.

Bodansky, M., *Principles of Peptide Synthesis*, Springer–Verlag, Berling, 1984.

Bomalaski et al., "Human Extracellular Recombinant Phospholipase $A_2$ Induces an Inflammatory Response in Rabbit Joints," *J. Immunol.*, 146: 3904–3910, 1991.

Bouzard et al., "Fluoronaphthyridines and Quinolones as Antibacterial Agents. 2. Synthesis and Structure–Activity Relationships of New 1–tert–Butyl 7–Substituted Derivatives," *J. Med. Chem.*, 33:1344–1352. (1990).

Braish et al., "Synthesis of (S,S)– and (R,R)–2–Alkyl–2, 5–diazabicyclo[2.2.1]heptanes," *J. Org. Chem.*, 55:1684–1687, 1990.

Bridges et al., "Conformationally Defined Neurotransmitter Analogues. Selective Inhibition of Glutamate Uptake by One Pyrrolidine–2,4–dicarboxylate Diastereomer," *J. Med. Chem.*, 34:717–725, 1991.

Burack et al., "Role of Lateral Phase Separation in the Modulation of Phospholipase $A_2$ Activity," *Biochemistry*, 32:583–589, 1993.

Campbell et al., "Inhibition of Phospholipase $A_2$; a Molecular Recognition Study," *J. Chem. Soc., Chem. Commun.*, 1560–1562, 1988.

Cho et al., "The Chemical Basis for Interfacial Activation of Monomeric Phospholipases $A_2$," *J. Biol. Chem.*, 263:11237–11241, 1988.

Cooper et al., "A Route to Optically Active Trisubstituted Pyrrolidines using Claisen Rearrangements of Azalactones," *Tetrahedron Letters*, 28:3031–3034, 1987.

Davidson et al., "1–Stearyl,2–Stearoylaminodeoxy Phosphatidylcholine, A Potent Reversible Inhibitor of Phospholipase $A_2$, " *Biochem. Biophyis. Res. Commun.*, 137:587–592, 1986.

Davidson et al., "Inhibition of Phosphilipase $A_2$ by Lipocortins and Calpactins," *J. Biol. Chem.*, 262:1698–1705, 1987.

Dennis, "Phospholipases," *The Enzymes*, Boyer, P. D., ed., New York: Academic Press, 16:307–353, Chapter 9, 1983.

Ecker et al., "Rational screening of oligonucleotide combinatorial libraries for drug discovery," *Nucleic Acids Res.*, 21:1853–1856, 1993.

Englisch et al., "Chemically Modified Oligonucleotides as Probes and Inhibitors," *Angewandte Chemie, International Edition*, 30:613–629, 1991.

Wery et al., "Structure of recombinant human rheumatoid arthritic synovial fluid phospholipase $A_2$ at 2.2 A resolution," *Nature*, 352:79–82, 1991.

Wright et al., "Large Scale Synthesis of Oligonucleotides via Phosphoramidite Nucleosides and a High–loaded Polystyrene Support," *Tetrahedron Letters*, 34:3373–3376, 1993.

Wyatt et al., "Combinatorially selected guanosine–quartet structure is a potent inhibitor of human immunodeficiency virus envelope–mediated cell fusion," *Proc. Natl. Acad. Sci. USA.*, 91:1356–1360, 1994.

Yang et al., "Studies on the status of lysine residues in phospholiapse $A_2$ from Naja naja atra (Taiwan cobra) snake venom," *Biochem. J.*, 262:855–860, 1989.

Yuan et al., "Synthesis and Evaluation of Phospholipid Analogues as Inhibitors of Cobra Venom Phospholipase $A_2$," *J. Am. Chem. Soc.*, 109:8071–8081, 1987.

PYRROLIDINE-CONTAINING MONOMERS AND OLIGOMERS

FIELD OF THE INVENTION

This invention is directed to pyrrolidine monomeric units and to oligomers constructed from them. The oligomers can be synthesized to have either random or predefined sequences of monomeric units and can be joined via phosphate linkages, including phosphorothioate and phosphodiester phosphate linkages. Each of the monomeric units can include a chemical moiety thereon for binding of the oligomeric structures to proteins, nucleic acid, and other biological targets. In preferred embodiments, the compounds of the invention act as inhibitors of enzymes such as phospholipase $A_2$ and are used for the treatment of inflammatory diseases including atopic dermatitis and inflammatory bowel disease.

BACKGROUND OF THE INVENTION

Phospholipases $A_2$ ($PLA_2$) are a family of enzymes that hydrolyze the sn-2 ester linkage of membrane phospholipids resulting in release of a free fatty acid and a lysophospholipid (see, Dennis, E. A., The Enzymes, Vol. 16, pp. 307–353, Boyer, P. D., ed., Academic Press, New York, 1983) Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (see, e.g., Dennis, ibid.; Glaser, et al., TiPs Reviews 1992, 14, 92; and Pruzanski, et al., Inflammation 1992, 16, 451).

All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath, et al., Inflammation 1988, 12, 549) or into the articular space of rabbits (Bomalaski, et al., J. Immunol. 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g., pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott, et al., Science 1990, 250, 1541). Recently, the crystal structure of $PLA_2$ from human synovial fluid has been solved (Wery, et al., Nature 1991, 352, 79). The structures clarify the role of calcium and amino acid residues in catalysis. The calcium acts as a Lewis acid to activate the scissile ester carbonyl and bind the lipid, and a His-Asp side chain dyad acts as general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft. (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site. (see, e.g., Achari, et al., Cold Spring Harbor Symp. Quant. Biol. 1987, 52, 441; Cho, et al., J. Biol. Chem. 1988, 263, 11237; Yang, et al., Biochem. J. 1989, 262, 855; and Noel, et al., J. Am. Chem. Soc. 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. The evidence favoring this hypothesis comes from studies revealing that rapid changes in $PLA_2$ activity occur concurrently with changes in the fluorescence of a membrane probe (Burack, et al., Biochemistry 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger, et al., FEBS Lett. 1989, 252, 73). These studies clearly show that $PLA_2$ binds exclusively at the boundary region between liquid and solid phase lipid.

While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e., phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (see, e.g., Yuan, et al., J. Am. Chem. Soc. 1987, 109, 8071; Lombardo, et al., J. Biol. Chem. 1985, 260, 7234; Washburn, et al., J. Biol. Chem. 1991, 266, 5042; Campbell, et al., J. Chem. Soc., Chem. Commun. 1988, 1560; and Davidson, et al., Biochem. Biophys. Res. Commun. 1986, 137, 587), reports describing in vivo activity are limited (see, e.g., Miyake, et al., J. Pharmacol. Exp. Ther. 1992, 263, 1302).

3

Traditional structure activity relationship type drug discovery gives unambiguous products but yet requires the preparation of numerous individual test candidates. The preparation of each structure requires significant amounts of time and resources. Another drug discovery approach, de novo design of active compounds based on high resolution enzyme structures, generally has not been successful. Yet another approach involves screening complex fermentation broths and plant extracts for a desired biological activity. The advantage of screening mixtures from biological sources is that a large number of compounds can be screened simultaneously, in some cases leading to the discovery of novel and complex natural products with activity that could not have been predicted otherwise. One disadvantage is that many different samples must be screened and numerous purifications must be carried out to identify the active component, which often is present only in trace amounts.

In order to maximize the advantages of each classical approach, new strategies for combinatorial unrandomization have been developed by several groups. Selection techniques have been used with libraries of peptides (see, e.g., Geysen, et al., *J. Immun. Meth.* 1987, 102, 259; Houghten, et al., *Nature* 1991, 354, 84; and Owens, et al., *Biochem. Biophys. Res. Commun.* 1991, 181, 402) and nucleic acids (see, e.g., Wyatt, et al., (in press) *Proc. Natl. Acad. Sci.* USA; and Ecker, et al., *Nucleic Acids Res.* 1993, 21, 1853). These selection techniques involve iterative synthesis and screening of increasingly simplified subsets of oligomers. In using these selection techniques, subsets are assayed for activity in either cell-based assays, or for binding or inhibition of purified protein targets.

One technique, called SURF (Synthetic Unrandomization of Randomized Fragments; see, e.g., Ecker, et al., ibid., involves the synthesis of subsets of oligomers containing a known residue at one fixed monomer position and equimolar mixtures of residues at all other positions. For a library of oligomers four residues long containing three monomers (A, B, C), three subsets would be synthesized (NNAN, NNBN, NNCN, where N represents equal incorporation of each of the three monomers). Each subset is then screened in a functional assay and the best subset is identified (e.g., NNAN). A second set of libraries is synthesized and screened, each containing the fixed residue from the previous round, and a second fixed residue (e.g. ANAN, BNAN, CNAN). Through successive rounds of screening and synthesis, a unique sequence with activity in the assay can be identified.

OBJECTS OF THE INVENTION

It is an object of this invention to provide novel pyrrolidine monomeric units.

It is another object of the invention to provide novel pyrrolidine monomeric units that can be incorporated into novel oligomeric structures.

It is a further object to provide novel pyrrolidine monomeric units that can be linked together via phosphorus-containing backbones.

It is still another object to provide novel pyrrolidine based oligomers that include a diversity of functional moieties thereon for binding to biological sites of interest.

4

BRIEF DESCRIPTION OF THE INVENTION

Compounds of the invention include monomeric compounds of structure I:

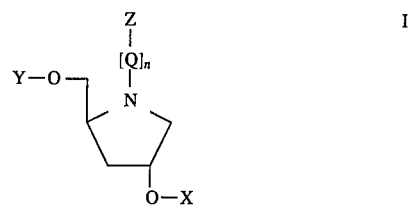

wherein:

X is H, a phosphate group, an activated phosphate group, an activated phosphite group, or a solid support;

Y is H or a hydroxyl protecting group;

Z is $L_1$, $L_1$-$G_1$, $L_2$, $L_2$-$G_2$, $NR_3R_4$, a nitrogen-containing heterocycle, a purine, a pyrimidine, a phosphate group, a polyether group, or a polyethylene glycol group;

$L_1$ is alkyl having 1 to about 20 carbon atoms, alkenyl having 2 to about 20 carbon atoms, or alkynyl having 2 to about 20 carbon atoms;

$L_2$ is aryl having 6 to about 14 carbon atoms or aralkyl having 7 to about 15 carbon atoms;

$G_1$ is halogen, $OR_1$, $SR_2$, $NR_3R_4$, $C(=NH)NR_3R_4$, $NHC(=NH)NR_3R_4$, $CH=O$, $C(=O)OR_5$, $CH(NR_3R_4)(C(=O)OR_5)$, $C(=O)NR_3R_4$, a metal coordination group, or a phosphate group;

$G_2$ is halogen, OH, SH, $SCH_3$, or $NR_3R_4$;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and, $R_4$ are, independently, H, alkyl having 1 to about 6 carbon atoms, or an amine protecting group;

$R_5$ is H, alkyl having 1 to about 6 carbon atoms, or an acid protecting group;

Q is $L_1$, $G_3$, $L_1$-$G_3$ or $G_3$-$L_1$-$G_3$;

$G_3$ is $C(=O)$, $C(=S)$, $C(O)$—O, $C(O)$—NH, $C(S)$—O, $C(S)$—NH or $S(O)_2$;

n is 0 or 1.

In preferred embodiments, Y is an acid labile hydroxyl blocking group such as a trityl, methoxytrityl, dimethoxytrityl or trimethoxytrityl group. X preferably is a phosphoramidite. In certain preferred embodiments, n is 1 and Q is carbonyl, thiocarbonyl, carboxy, acetyl or succinyl.

In one preferred group of compounds, Z includes a nitrogen-containing heterocycle such as an imidazole, pyrrole or carbazole ring. In a further preferred group, Z includes a purine or a pyrimidine nucleobase such as adenine, guanine, cytosine, uridine or thymine. In another preferred group of compounds, Z includes an unsubstituted or amine-substituted alkyl group, or an aryl group having 6 to about 20 carbon atoms. In yet another preferred groups of compounds, Z includes fluorenylmethyl, phenyl, benzyl, alkyl-substituted benzyl, polyethylene glycol, glutamyl, or $NR_3R_4$ groups.

Further compounds of the invention include oligomeric compounds of structure II:

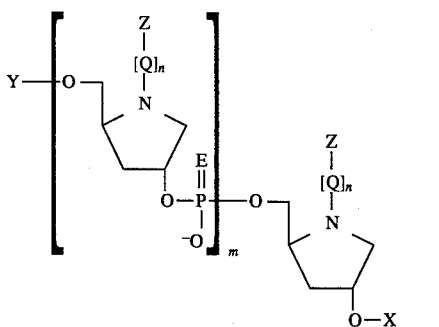

wherein:
X is H, a phosphate group, an activated phosphate group, an activated phosphite group, a solid support, a conjugate group, or an oligonucleotide;

Y is H, a hydroxyl protecting group, a conjugate group or an oligonucleotide;

E is O or S;

Z is $L_1$, $L_1$–$G_1$, $L_2$, $L_2$–$G_2$, $NR_3R_4$, a nitrogen-containing heterocycle, a purine, a pyrimidine, a phosphate group, a polyether group, or a polyethylene glycol group;

$L_1$ is alkyl having 1 to about 20 carbon atoms, alkenyl having 2 to about 20 carbon atoms, or alkynyl having 2 to about 20 carbon atoms;

$L_2$ is aryl having 6 to about 14 carbon atoms or aralkyl having 7 to about 15 carbon atoms;

$G_1$ is halogen, $OR_1$, $SR_2$, $NR_3R_4$, $C(=NH)NR_3R_4$, $NHC(=NH)NR_3R_4$, $CH=O$, $C(=O)OR_5$, $CH(NR_3R_4)(C(=O)OR_5)$, $C(=O)NR_3R_4$, a metal coordination group, or a phosphate group;

$G_2$ is halogen, OH, SH, $SCH_3$, or $NR_3R_4$;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and $R_4$ are, independently, H, alkyl having 1 to about 6 carbon atoms, or an amine protecting group;

$R_5$ is H, alkyl having 1 to about 6 carbon atoms, or an acid protecting group;

Q is $L_1$, $G_3$, $L_1$–$G_3$ or $G_3$–$L_1$–$G_3$;

$G_3$ is C(=O), C(=S), C(O)—O, C(O)—NH, C(S)—O, C(S)—NH or $S(O)_2$;

n is 0 or 1; and m is 1 to about 50, preferably 1 to about 25.

Further compounds of the invention include chimeric oligomeric compounds having a central region comprising a phosphodiester or a phosphorothioate oligodeoxynucleotide interspaced between flanking regions comprising the above-described monomeric or oligomeric structures.

The invention further includes processes for preparing randomized oligomeric compounds including the steps of selecting a group of monomers as described above and covalently bonding at least two of the monomers of said group. In preferred processes, the Z moiety of at least one monomer of said group is different from the Z moiety of another monomer of said group.

The compounds of the invention can be used as inhibitors of various enzymes including phospholipase $A_2$ enzyme. As inhibitors of phospholipase $A_2$, the compounds are useful for the treatment of inflammatory diseases including atopic dermatitis and inflammatory bowel disease. The oligomeric compounds of the invention can be used in diagnostics since they are capable of specifically hybridizing to nucleic acids of interest in the etiology of diseases. The compounds of the invention also can be used as research probes and primers, especially for the study of enzyme biochemistry and protein-nucleic acid interactions.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1:
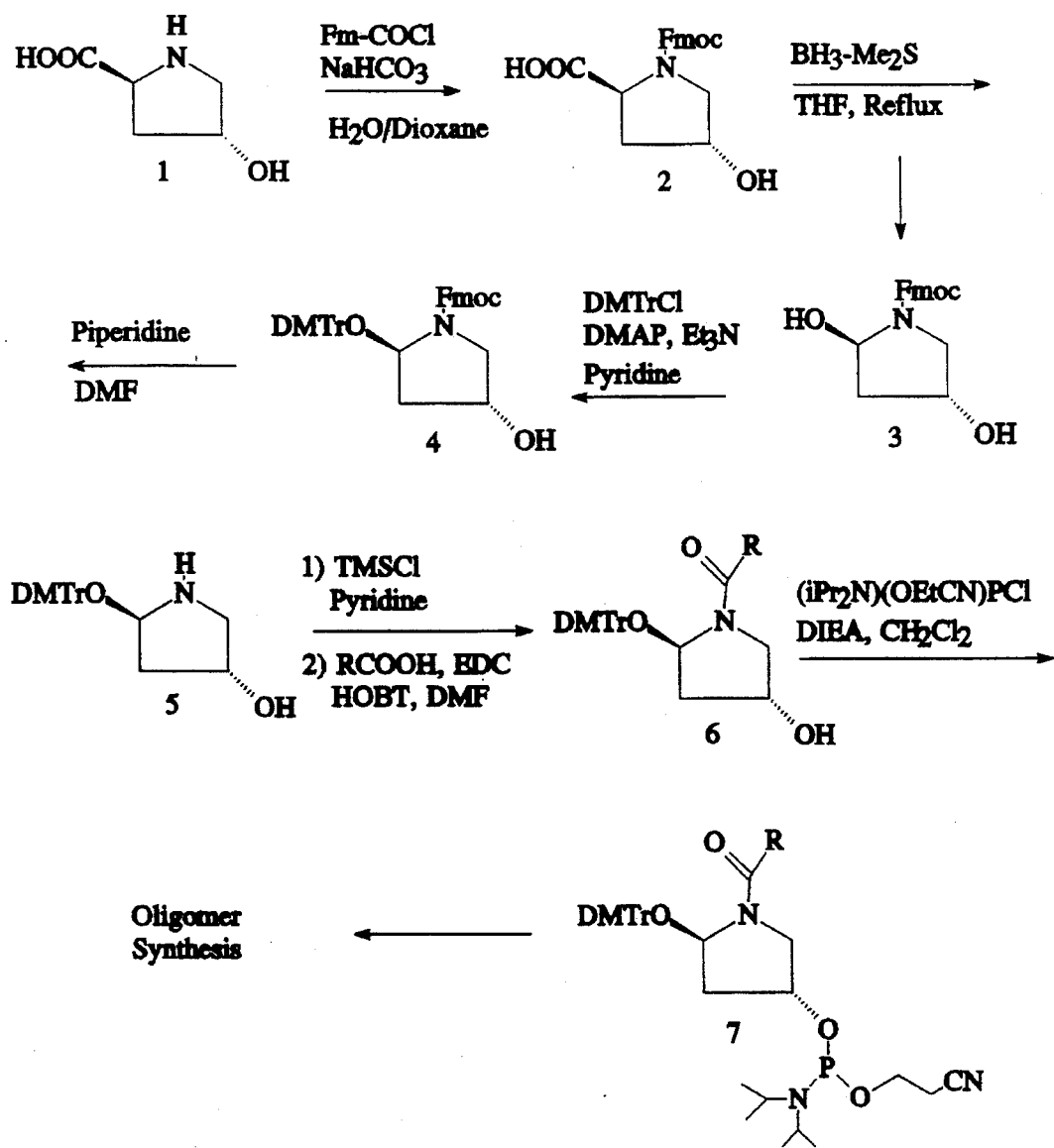
FIG. 1 describes synthetic processes for oligomeric compounds according to the invention.

The monomeric compounds of the invention each include a pyrrolidine moiety that, in turn, bears a number of functional groups. Certain of these groups are used to link adjacent pyrrolidine moieties and form oligomeric structures. Typically, the groups used to effect such linkage are primary and secondary hydroxyl groups. During oligomer synthesis, the primary hydroxyl group typically is blocked with a protecting group and the secondary hydroxyl group is reacted with an activated phosphate group such as a β-cyanoethyl phosphoramidate group. As used herein, the term activated phosphate group is intended to denote a phosphate group that bears a chemical modification thereon to enhance its reactivity with nucleophiles. Similarly, the term activated phosphite group denotes a phosphite group that bears a chemical modification to enhance its reactivity with nucleophiles. Numerous such modifications are known in the art.

The monomeric compounds of the invention preferably are covalently bound using phosphate linkages. This permits coupling via either solution phase or solid phase chemistries. Representative solution phase techniques are described in U.S. Pat. No. 5,210,264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.) A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods. This allows for synthesis of the preferred phosphodiester or phosphorothioate phosphate linkages depending upon oxidation conditions selected. Other phosphate linkages can also be generated. These include phosphorodithioates, phosphotriesters, alkyl phosphonates, phosphoroselenates and phosphoamidates.

The pyrrolidine moieties bear functional groups in addition to those that form inter-pyrrolidine linkages. When the monomeric compounds are linked together, these functional groups provide diverse properties ("diversity") to the resulting oligomeric compounds. The functional groups include hydrogen-bond donors and acceptors, ionic moieties, polar moieties, hydrophobic moieties, aromatic centers, and electron-donors and acceptors. Together, the properties of the individual monomers contribute to the uniqueness of the oligomers in which they are found. Thus, a library of such oligomers would have a myriad of properties, i.e., "diversity." Collectively, the properties of the individual monomers that together for form an oligomer contribute to the uniqueness of such oligomer and impart certain characteristics thereto for interaction with cellular, enzymatic or nucleic acid target sites.

Nitrogen heterocycles suitable for use as the functional group include imidazole, pyrrole, pyrazole, indole, 1H-indazole, α-carboline, carbazole, phenothiazine, and phenoxazine groups. A more preferred group of nitrogen heterocycles includes imidazole, pyrrole, and carbazole groups. Imidazole groups are especially preferred.

Purines and pyrimidines according to the invention include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et *Angewandte Chemie, International Edition* 1991, 30, 613.

Alkyl, alkenyl, and alkynyl groups according to the invention include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Aryl groups according to the invention include but are not limited to substituted and unsubstituted aromatic hydrocarbyl groups such as phenyl and naphthyl groups. Aralkyl groups include but are not limited to groups having both aryl and alkyl functionality, such as benzyl and xylyl groups.

Metal coordination groups according to the invention include but are not limited to hydroxamic acids, catecholamide, acetylacetone, 2,2'-bipyridine, 1,10-phenanthroline, diacetic acid, pyridine-2-carboxamide, isoalkyldiamine, thiocarbamato, oxalate, glycl, histidyl and terpyridyl. Other metal coordination groups are known, as for example see Mellor, D. P., *Chemistry of Chelation and Chelating Agents in International Encyclopedia of Pharmacology and Therapeutics*, Section 70, The Chelation of Heavy Metals, Levine, W. G. Ed., Pergamon Press, Elmford, N.Y., 1979.

Solid supports according to the invention include controlled pore glass (CPG), oxalyl-controlled pore glass (see, e.g., Alul, e al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene.

A number of substituent groups can be introduced into compounds of the invention in a protected (blocked) form and subsequently de-protected to form a final, desired compound. In general, protecting groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. For example, amino groups can be protected as phthalimido groups or as 9-fluorenylmethoxycarbonyl (FMOC) groups and carboxyl groups can be protected as fluorenylmethyl groups. Representative hydroxyl protecting groups are described by Beaucage, et al., Tetrahedron 1992, 48, 2223. Preferred hydroxyl protecting groups are acid-labile, such as the trityl, monomethoxytrityl, dimethoxytrityl, and trimethoxytrityl groups.

Substituent groups according to the invention include but are not limited to halogen (Cl, Br, F), hydroxyl (OH), thiol (SH), keto (C=O), carboxyl (COOH), ethers, thioethers, amidine (C(=NH)NR$_3$R$_4$), guanidine (NHC(=NH)NR$_3$R$_4$, glutamyl CH(NR$_3$R$_4$)(C(=O)OR$_5$), nitrate (ONO$_2$), nitro (NO$_2$), nitrile (CN), trifluoromethyl (CF$_3$), trifluoromethoxy (OCF$_3$), O-alkyl, S-alkyl, NH-alkyl, N-dialkyl, O-aralkyl, S-aralkyl, NH-aralkyl, amino (NH$_2$), azido (N$_3$), hydrazino (NHNH$_2$), hydroxylamino (ONH$_2$), sulfoxide (SO), sulfone (SO$_2$), sulfide (S–), disulfide (S—S), silyl, heterocyclic, alicyclic and carbocyclic. Preferred substituents include halogens, alcohols and ethers (OR$_1$), thiols and thioethers (SR$_2$), amines (NR$_3$R$_4$), amidines [C(=NH)NR$_3$R$_4$], guanidines [NHC(=NH)NR$_3$R$_4$], aldehydes (CH=O), acids [C(=O)OH], esters [C(=O)OR$_5$], amides [C(=O)NR$_3$R$_4$] and glycine [CH(NH$_2$)(C(=O)OH)].

In preferred embodiments, Z includes an aminoethyl, carboxyethyl, adenylmethyl, thyminylmethyl, imidazolylmethyl, benzyl, 4-hexylbenzyl, myristyl, isopropyl, or tetraethylene glycol group. Z can be directly attached to the pyrrolidine ring or can be attached via a tether, Q. Preferred tethers include alkyl and acyl (carbonyl-containing) groups. Preferred acyl groups include carbonyl, thiocarbonyl, carboxy, acetyl, and succinyl groups.

The compounds of the invention can include conjugate groups covalently bound to primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenanthroline, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. patent application Ser. No. 116,801, filed Sept. 3, 1993, and U.S. Patent No. 5,218,105. Each of the foregoing is commonly assigned with this application. The entire disclosure of each is incorporated herein by reference.

Monomeric compounds of the invention can be used to prepare oligomeric compounds having either preselected sequences or sequences determined via combinatorial strategies. One useful combinatorial strategy is the above-noted SURF strategy, which is disclosed and claimed in U.S. patent application Ser. No. 749,000, filed Aug. 23, 1991, and PCT Application US92/07121, filed Aug. 21, 1992, both of which are commonly assigned with this application. The entire disclosure of these applications are herein incorporated by reference.

Illustrative of the SURF strategy is a 2'-O-methyl oligonucleotide library (see, Ecker et. al., ibid.) shown in Table I, below. Table I describes the selection of a 2'-O-methyl oligonucleotide for binding to an RNA hairpin. The $K_D$'S, i.e., the binding constants, were determined by gel shift. "X" is used to indicate the position being varied and underlining is used to indicate positions that become fixed during successive iterations of the SURF strategy.

TABLE I

| Subsets | $K_D$ (mM) | | | |
|---|---|---|---|---|
| | X = A | X = C | X = G | X = T |
| Round 1 NNNNXNNNN | 22 | 10 | >100 | >100 |
| Round 2 NNNNCNXNN | >10 | 4 | >10 | >10 |
| Round 3 NNXNCNCNN | >10 | 0.5 | >10 | >10 |
| Round 4 NNCXCNCNN | >10 | 0.15 | >10 | >10 |
| Round 5 NNCCCXCNN | 0.08 | >1 | 0.4 | >1 |
| Round 6 NNCCCACXN | 0.05 | >0.5 | 0.08 | >0.5 |
| Round 7 NXCCCACAN | >0.1 | >0.1 | 0.03 | >0.1 |
| Round 8 NGCCCACAX | 0.05 | 0.02 | 0.05 | 0.04 |
| Round 9 XGCCCACAC | 0.03 | 0.05 | 0.02 | 0.01 |

This SURF strategy has not been used for libraries except those that employ naturally-occurring nucleotides as phosphodiesters or phosphorothioates as monomeric units. Other combinatorial strategies have only been used for libraries that employ amino acids as monomeric units.

One aspect of the present invention is the inclusion of monomeric compounds having structure I in the above-described SURF strategy. The functional groups appended to these monomeric compounds can be incorporated into the libraries while retaining the advantages of automated phosphoramidite oligomer synthesis. These functional groups can effect interactions of the following types: hydrogen-bond donor and acceptor, ionic, polar, hydrophobic, aromatic, and electron donors and acceptors. Preferred functional groups include aminoethyl, carboxyethyl, adenylmethyl, thyminyl-methyl, imidazolylmethyl, benzyl, myristyl, isopropyl, and tetraethylene glycol groups.

One advantage of the present invention is that the simple design of monomeric compounds of the inventions allows for combining rational drug design with screen mechanisms for thousands of compounds. This is achieved by using the compounds of the invention in a combinatorial techniques such as the SURF strategies.

In one preferred embodiment, functional groups appended to the monomeric compounds of the invention are selected for their potential to interact with, and preferably inhibit, the enzyme $PLA_2$. Thus, the compounds of the invention can be used for topical and/or systematic treatment of inflammatory diseases including atopic dermatitis and inflammatory bowel disease. In selecting the functional groups, advantage can be taken of $PLA_2$'s preference for anionic vesicles over zwitterionic vesicles. In selecting the backbone that bears these functional groups, further advantage can be taken of fact that the natural substrate of $PLA_2$ contains a phosphate group. Therefore, phosphodiester or phosphorothioate and other phosphate linked oligomers preferably are selected, providing a negatively charged compound for binding with the positively charged interfacial binding site of $PLA_2$.

Certain compounds of the invention include aromatic functional groups to facilitate binding to the cleft of the $PLA_2$ enzyme. (see, Oinuma, et al., *J. Med. Chem.* 1991, 34, 2260; Marki, et al., *Agents Actions* 1993, 38, 202; and Tanaka, et al., *J. Antibiotics* 1992, 45, 1071). Benzyl and 4-hexylbenzyl groups are preferred aromatic groups. The compounds of the invention can further include hydrophobic functional groups such as tetraethylene glycol groups. Since the $PLA_2$ enzyme has a hydrophobic channel, hydrophobicity is believed to be an important property of inhibitors of the enzyme.

In certain embodiments of the invention, hydroxy pyrrolidine phosphoramidite monomeric compounds having structure I are incorporated into libraries of oligomeric compounds and increasingly less complex subsets of oligomers are identified in combinatorial screening techniques such as the above-described SURF technique by successive rounds of screens. In one preferred embodiment, a library of oligomeric compounds functionalized with aminoethyl, carboxyethyl, adenyl-methyl, thyminylmethyl, tetraethylene glycol, imidazolyl-methyl, benzyl, isopropyl, myrismyl or 4-hexylbenzyl groups are prepared and assayed for inhibition of $PLA_2$ activity. The $PLA_2$ assay can be effected using a combinatorial screening strategy such as the SURF strategy. For this assay, the oligomer libraries are screened for inhibition of human type II $PLA_2$ enzymatic activity. Typically, these libraries contain about 8000 different compounds. Successive iterations of the SURF technique is effected to select unique oligomers from the library. The libraries additionally can be screened in other in vitro assays to determine further mechanisms of inhibition.

Upon identification of oligomers in a first phase of screening, further modifications can be made to the contents of the oligomer libraries. For example, if a first iteration of screening results in an active compound that contains a benzyl group, then in subsequent iterations of the screen this aromatic residue can then be varied using substituted benzyl groups. In this way, structural activity is identified in a stepwise manner to define potent inhibitors of the enzymatic activity.

To maximize the identification of a tight binding oligomeric inhibitor of $PLA_2$ via a combinatorial approach, an array of functional groups typically are included in a randomized library. The oligomers are assembled in a manner analogous to oligonucleotide synthesis by the coupling of monomeric, phosphoramidate units wherein the normal nucleotide structure is replaced by more diverse chemical groups. In some of the monomeric units, the nucleobases of nucleotides have been retained. In other, the nucleobases are replaced with other functional groups selected to provide different ligand-ligand interactions than that provided by the nucleobases. The sugar moiety of a normal nucleotide is replaced by a hydroxy pyrrolidine unit, i.e. a prolinol, to form a unique prolinol-phosphate backbone. This methodology provides for a convergent preparation of a large number of monomers bearing a wide variety of functional groups. Where necessary, functional groups are protected with base labile protecting groups to allow one-step deprotection of the oligomer upon completion of the synthesis.

As noted above, monomeric compounds having structure I can be linked with one another to form homopolymeric structures or they can be linked with nucleotides and/or other moieties to form heteropolymeric structures. For example, chimeric structures can be formed that include one or more regions or "stretches" of the monomeric units of invention joined to one or more regions or "stretches" of naturally occurring or synthetic oligonucleotides or to other synthetic or natural oligomeric compounds such as peptides, peptoids, peptide nucleic acids, oligo and/or polysaccharides. Further, oligomeric compounds having structure II can be incorporated into chimeric structures along with the compounds disclosed in the patent application entitled "Monomeric Diols And Phosphate Linked Oligomers Formed Therefrom," bearing attorney docket ISIS-0868 and the patent application entitled "Oligonucleotide Mimics Having Nitrogen-Containing Linkages," bearing attorney docket ISIS-1014. The foregoing patent applications are filed concurrently with this application, are commonly assigned, and are incorporated herein by reference.

In one embodiment of the invention, oligomeric compounds are synthesized as shown in FIG. 1. This synthetic strategy emphasizes attachment of widely different functional groups to a rigid hydroxyprolinol intermediate. Each monomer unit contains a primary hydroxyl that is protected as a dimethoxytrityl (DMT) ether and a secondary hydroxyl that is converted to a cyanoethyl-diisopropylamino phosphoramidite. Trans-hydroxyproline 1 is protected as the fluorenylmethyl carbamate (Fmoc), and the carboxylate function is reduced using borane in refluxing tetrahydrofuran (THF). Diol 3 is then selectively protected at the primary hydroxyl as a DMT, and the Fmoc group of 4 is removed using piperidine in dimethylformamide (DMF). A substituted carboxylic acid is then covalently linked to the nitrogen of intermediate 5 using standard peptide coupling methods (see Bodansky, M., *Principles of Peptide Synthesis*, 1984, Springer-Verlag, Berlin). Functional groups (R) that require protection are derivatized using base labile protecting groups. Monomers 6 are converted to the phosphoramidites 7 under standard conditions (see *Oligonucleotide synthesis, a practical approach*, Gait, M. J. Ed., 1984, IRL Press, Oxford). These phosphoramidites are then oligomerized, either in predetermined sequences using standard oligonucleotide type synthetic procedures on a DNA synthesizer, a solution phase reaction, or combinatorial techniques such as the above-described SURF technique.

Monomer units bearing protected or unprotected functional groups are prepared as per procedures described in the examples provided below. If the functional groups is such that it will react with other moieties or reagents during phosphitylation or oligomerization, the functional group is appropriately protected with a protecting group. Such protecting group is then removed upon completion of the synthesis of oligomeric compound.

To detect an active sequence generated via a combinatorial technique, the concentration of the active molecule is selected to be of sufficiently great that the molecule can be detected within the sensitivity of the chosen assay. As will be recognized, the number of unique oligomer sequences within a subset produced via a combinatorial technique depends on the length of the oligomer and the number of different monomers employed. The number of sequences can be determined by raising the number of monomers to a power equal to the number of random positions. This is illustrated in Table II. Table II also indicates the concentration of each sequence when the subset concentration is 100 µM, a typical high-test concentration. We have found that the number of monomers and their length can be based upon an estimate of the expected $IC_{50}$ (i.e., a concentration at which 50% of enzyme activity is inhibited) that is desirable in a final oligomeric compound. For an expected $IC_{50}$ of 100 nM, the complexities shown in Table II are acceptable, that is, the libraries shown in Table II have complexities that would allow detection of a unique sequence with an $IC_{50}$ of about 100 nM or less.

TABLE II

| | Complexity of Libraries | |
|---|---|---|
| Length | Sequences Per Subset | nM Each Sequence At 100 µM Subset |
| 5 Monomers | | |
| 4-mer | 125 | 800 |
| 5-mer | 625 | 160 |
| 6 Monomers | | |
| 4-mer | 216 | 463 |
| 5-mer | 1,296 | 77 |
| 7 Monomers | | |
| 4-mer | 343 | 291 |
| 8 Monomers | | |
| 4-mer | 512 | 195 |
| 10 Monomers | | |
| 4-mer | 1,000 | 100 |

If five monomers are selected for a library, then the library will have a length of five monomer units, XNNNN, where N is an equal molar mixture of monomer units and X is a different monomer unit in each of the five subsets. For ease in synthesis, the fixed position can be selected as the right end of the molecule. After assay for inhibition of $PLA_2$ activity as described below, position X is fixed with the residue giving the greatest inhibition and the next subset is synthesized and screened. The fixed position then shifts towards the left end of the oligomer as unrandomization proceeds. Five rounds of synthesis and screening are required to determine a unique inhibitor.

The monomer units of the invention are linked to form oligomeric compounds using standard phosphoramidite chemistry that is used for standard synthesis of oligonucleotides. Since the coupling rates of functionalized prolinol monomers may vary, the reactivity of the individual monomers can adjusted such that equal molar incorporation of each monomer at each randomized position is effected. Adjusting for the reactivity of the monomers can be effected as in Examples 66 and 67. A further technique for effecting such adjustment is also disclosed in the United States patent application entitled "Random Oligonucleotide Libraries And Methods Of Making The Same," bearing attorney docket number ISIS-1009. The foregoing patent application is being filed concurrently with this application, is commonly assigned, and is incorporated herein by reference.

In a SURF screening strategy the amount of oligomer is selected such that the concentration of each subset in the initial round of screening is relatively high (about 100 µM). It is presently preferred to synthesize oligomers using a DNA synthesizer. On such synthesizers the oligomers are most conveniently synthesized on a 1 to 4 µmol scale. Given the concentration of a subset of libraries at about 100 µm, the assays preferably are performed in a small volume of less than about 200 µL.

Exemplary compounds of the invention are prepared in the following examples, which are not intended to be limiting.

EXAMPLE 1

N-Fmoc-trans-4-Hydroxy-L-Proline (2).

Hydroxyproline, 1, (5.00 g, 38.2 mmol) and $NaHCO_3$ (8.00 g, 95.2 mmol) were suspended in 150 ml $H_2O$/Dioxane (1:1). Fluorenylmethyl chloroformate (11.4 g, 44.0 mmol) in 25 ml toluene was added dropwise. The temperature of the reaction was not allowed to rise above 25° C. during the addition. The mixture was stirred vigorously overnight, and then quenched with 50 ml saturated $NaHCO_3$ solution and 50 ml water. The solution was then extracted with 100 ml diethyl ether. The aqueous layer was acidified to pH 1 with concentrated HCl, and extracted twice with ethyl acetate, and the organic extracts washed with brine. The solution was dried with $MgSO_4$, filtered and the solvent removed in vacuo. The pure product crystallized from the concentrated solution. Yield: 13.4 g (100%). $^1H$ NMR: ($CDCl_3$, 200 MHz) $\delta 7.75$–7.15 (8H, m, ArH), 4.55–4.05 (5H, m, $ArCHCH_2$, H2, H4), 3.65–3.45 (2H, m, 2 H5), 2.35–2.10 (2H, m, 2 H3).

EXAMPLE 2

$N^1$-Fmoc-3-Hydroxypyrrolidine-5-Methanol (3).

To a solution of 2 (13.4 g, 38.1 mmol) in 250 ml THF was added borane-methyl sulfide (78 mmol, 5.78 g, 7.22 ml) dropwise at room temperature. After the evolution of $H_2$ had ceased, the solution was heated to reflux with mechanical stirring. After 1 hour a white precipitate had formed. Methanol was carefully added, and the resulting solution refluxed for a further 15 minutes. The solution was cooled to room temperature, the solvents evaporated under reduced pressure, and the residual gum coevaporated with 2×100 ml methanol (MeOH). The resulting crystalline product weighed 12.0 g (35.3 mmol, 93%). $^1H$ NMR: ($CDCl_3$, 200 MHz) $\delta 7.85$–7.25 (8H, m, ArH), 4.50–4.10 (5H, m, $ArCHCH_2$, H3, H5), 3.80–3.40 (4H, m, 2 H2, 2 H6), 2.15–1.95 (1H, m, H2a), 1.80–1.60 (1H, m, H2b).

EXAMPLE 3

$N^1$-Fmoc-5-Dimethoxytrityloxymethyl-3-Hydroxypyrrolidine (4).

The diol 3 (12.0 g, 35.3 mmol) was coevaporated with dry pyridine (2×50 ml), redissolved in 200 ml dry pyridine, and cooled in an ice bath. Dimethoxytrityl chloride (13.6 g, 38 mmol) was added in portions over 15 minutes, and the solution stirred at room temperature overnight. Methanol was then added (10 ml), and the solvent removed under reduced pressure. The resulting gum was redissolved in toluene (100 ml), filtered to remove the pyridinium hydrochloride and taken to dryness again. The residue was triturated with ether/hexane to produce a tan solid, and chromatographed (0 to 1.5% MeOH/$CH_2Cl_2$) to give the product (14.85 g, 23 mmol, 66%). Alternatively, the product could be crystallized from 2:1 hexane/ethyl acetate.

EXAMPLE 4

5-Dimethoxytrityloxymethyl-3-Hydroxypyrrolidine (5).

To a solution of carbamate 4 (3.40 g, 5.30 mmol) in 15 ml DMF was added piperidine (1.09 ml, 0.935 g, 11.0 mmol). The solution was stirred at room temperature for 1 hour, water (100 ml) added, and the aqueous solution extracted with ethyl acetate (2×75 ml). The organic extracts were washed with aqueous $NaHCO_3$, brine, dried with $MgSO_4$ and evaporated. The residue was purified by flash using a gradient of 1→3% MeOH in $CH_2Cl_2$ containing 0.5% triethylamine. Pure product was obtained (1.86 g, 84%). $^1H$ NMR: ($CDCl_3$, 200 MHz) $\delta 7.42$–6.80 (13H, ArH), 4.35 (1H, m, H5), 3.77 (6H, s, $2OCH_3$), 3.62 (1H, m, H3), 3.13–2.88 (4H, m, 2 H6, 2 H2), 1.87 (1H, q, H4a), 1.65 (1H, m, H4b).

EXAMPLE 5

$N^1$-Palmitoyl-5-Dimethoxytrityloxymethyl-3-Hydroxypyrrolidine

To the amino alcohol 5 (0.50 g, 1.19 mmol) dissolved in 5 ml dry pyridine was added chlorotrimethylsilane (0.227 ml, 194 mg, 1.79 mmol), with stirring for 1 hour. The carboxylic acid component (e.g. palmitic acid, 359 mg, 1.40 mmol), hydroxybenzotriazole (209 mg, 1.55 mmol) and dimethyl-aminopropyl-ethylcarbodiimide (EDC) (281 mg, 1.80 mmol) were dissolved in 5 ml DMF (if necessary 5 ml $CH_2Cl_2$ co-solvent added) and stirred for 1 hour. This solution was then added to the pyridine solution of 5, and the solution stirred until complete disappearance of the starting material. The reaction was stopped by addition of 5 ml sat $NaHCO_3$ and after 15 minutes the solution was diluted with water (100 ml), extracted with ethyl acetate (2×75 ml), washed with $NaHCO_3$, brine, dried and evaporated. The product was purified by silica gel chromatography using ethyl acetate/hexane (EtOAc/Hex) as eluant. $^1H$ NMR: ($CDCl_3$, 200 MHz) (2 rotamers, 3'-O-TMS) $\delta 7.43$–7.13, 6.88–6.74 (13 Ar—H), 4.67, 4.51, 4.40, 4.13 (4 m, 2H, H3, H5), 3.90–3.67 (m, 1H, H2a), 3.80 (s, 6H, $OCH_3$), 3.45 (m, 2H, H2b, H6a), 3.12 (m, 1H, H6b), 2.34–1.78 (m, 4H, H4a, H4b, $COCH_2$), 1.65, 1.25 (2 s, 26H, $CH_2$), 0.87 (t, $CH_3$), 0.10 (s, 9H, $OSi(CH_3)_3$).

EXAMPLE 6

$N^1$-Isobutyroyl-5-Dimethoxytrityloxymethyl-3-Hydroxypyrrolidine

This compound was prepared as per the procedure described in Example 5 by the use of isobutyric acid as the carboxylic acid component. $^1H$ NMR: ($CDCl_3$, 200 MHz) (2 rotamers, 3'-O-TMS) $\delta 7.43$–7.13, 6.88–6.74 (13 Ar—H), 4.75, 4.52, 4.37, 4.16 (4 m, 2H, H3, H5), 3.78 (s, 6H, $OCH_3$), 3.88–3.78 (m, 1H, H2a), 3.68–3.34 (m, 2H, H2b, H6a), 3.28–2.93 (m, 1H, H6b), 2.67, 2.58 (2 m, 1H, $COCH(Me)_2$)), 2.18–1.80 (2 m, 2H, H4a, b), 1.15, 0.98 (2 q, 6H, $COCH(CH_3)_2$), 0.10 (d, 9H, $OSi(CH_3)_3$).

EXAMPLE 7

$N^1$-Phenylacetyl-5-Dimethoxytrityloxymethyl-3-Hydroxypyrrolidine

This compound was prepared as per the procedure described in Example 5 by the use of phenylacetic acid as the carboxylic acid component. $^1H$ NMR: ($CDCl_3$, 200 MHz) (2 rotamers, 3'-O-TMS) $\delta 7.43$–7.13, 6.88–6.74 (13 Ar—H), 4.67, 4.49, 4.37, 4.13 (4 m, 2H, H3, H5), 3.78 (s, 6H, $OCH_3$), 3.78–3.50 (m, 2H, H2a, b), 3.66, (s, 2H, $CH_2Ar$) 3.35 (q, 1H, H6a), 3.12 (m, 1H, H6b), 2.14–1.70 (m, 2H, H4a, b), 0.10 (d, 9H, $OSi(CH_3)_3$).

EXAMPLE 8

Succinic Acid Monofluorenylmethyl Ester.

Fluorenylmethanol (0.90 g, 4.5 mmol) and dimethylaminopyridine (50 mg) were dissolved in 10 ml dry pyridine. Succinic anhydride (0.50 g, 5.0 mmol) was added and the solution stirred overnight. The solvent was removed under reduced pressure, sodium bicarbonate added (50 ml), the solution extracted with ethyl acetate (50 ml), and the organic layer discarded. The aqueous layer was acidified to pH 2, extracted with ethyl acetate (2×100 ml), washed with brine, and the solvent removed under reduced pressure. The residue was purified by flash chromatography (ethyl acetate/hexane 2:1 as eluant) to give 0.86 g product (2.9 mmol, 64%). $^1$H NMR: (CDCl$_3$, 200 MHz) δ7.8–7.26 (8H, m, ArH), 4.43 (2H, d, J=6.5 Hz, CHCH$_2$OCO), 4.23 (1H, t, J=6.5 Hz, CHCH$_2$OCO), 2.70 (4H, s, OCOCH$_2$CH$_2$COO).

EXAMPLE 9

$N^1$-(Fluorenylmethylsuccinoyl)-5-Dimethoxytrityloxymethyl-3-Hydroxypyrrolidine This compound was prepared as per the procedure described in Example 5 using succinic acid monofluorenylmethyl ester as the carboxylic acid component. $^1$H NMR: (CDCl$_3$, 200 MHz) (2 rotamers) δ7.80–6.80 (21 Ar—H), 4.62, 4.46, 4.21 (3 m, 2H, H3, H5), 4.41–4.28 (m, 3H, CH$_2$CH), 3.78 (s, 6H, OCH$_3$), 3.92, 3.71, 3.54, 3.41, 3.16 (5 m, 4H, H2a,b, H6a,b), 2.88–2.75 (m, 4H, COCH$_2$H$_2$CO), 2.50–1.93 (4m, 2H, H4a, b).

EXAMPLE 10

(N1-Thymidine)-2-Acetic Acid

Methyl bromoacetate (25.5 g, 15.2 ml, 160 mmol) was added to a suspension of K$_2$CO$_3$ (44.2 g, 320 mmol) and thymidine (20.2 g, 160 mmol) in 500 ml dry DMF with stirring overnight. The suspension was filtered and the solvent removed under reduced pressure. The residue was suspended in 120 ml H$_2$O and 30 ml 4N HCl, stirred for 30 minutes and filtered again. The solid was suspended in 250 ml H$_2$O, to which was added 100 ml 2.5M NaOH. The solution was heated to boiling, cooled and acidified to pH 1 with concentrated HCl. The precipitate was dried in vacuo to give 13,6 g (73.6 mmol, 46%) pure product. $^1$H NMR: (DMSO-d6, 200 MHz) δ7.48 (s, 1H, H6), 4.37 (s, 2H, CH$_2$), 1.76 (s, 3H, CH$_3$).

EXAMPLE 11

$N^1$-[(N1-Thymidine)-2-acetyl]-5-Dimethoxytrityloxymethyl-3-Hydroxypyrrolidine

This compound was prepared as per the procedure described in Example 5 using thymidine-2-acetic acid as the carboxylic acid component. $^1$H NMR: (DMSO-d6, 200 MHz) (2 rotamers) δ7.50–6,80 (C6H, 13 Ar—H), 4.60–4.40, 4.28 (m, 3H, COCH$_2$, H5), 4.15 (m, 1H, H3), 3.70 (s, 6H, OCH$_3$), 3.66 (m, 1H, H2a), 3.45–2.94 (m, 4H, H2a,b, H6a,b), 2.08–1.82 (m, 2H, H4a, H4b), 1.65 (s, 3H, (C5)CH$_3$).

EXAMPLE 12

N-Fmoc-3-Aminopropionic Acid.

Sodium bicarbonate (2.52 g, 30 mmol) and 3-aminopropionic acid (1.00 g, 11.2 mmol) were dissolved in 50 ml water and 50 ml dioxane was added. A solution of fluorenylmethyl chloroformate (3.10 g, 12.0 mmol) in 50 ml dioxane was added dropwise with stirring. After 6 hours the solution was diluted with water (100 ml) and saturated bicarbonate solution (50 ml), extracted once with diethyl ether, and the aqueous layer acidified to pH 2 with concentrated HCl. The cloudy solution was extracted with ethyl acetate (2×100 ml), washed with brine and dried with MgSO$_4$. After evaporation a mixture of the title product and the peptide dimer was obtained. The pure product was obtained by flash chromatography. $^1$H NMR: (CDCl$_3$, 200 MHz) δ7.95–7.26 (8H, m, ArH), 7.40–7.15 (3H, m, CHCH$_2$O), 3.20 (2H, t, J=8 Hz, CH$_2$N), 2.40 (2H, t, J=8 Hz, HOOCCH$_2$).

EXAMPLE 13

$N^1$-(N-Fmoc-3-Aminopropionoyl)-5-Dimethoxytrityloxymethyl-3-Hydroxypyrrolidine This compound was prepared as per the procedure described in Example 5 using N-Fmoc-3-aminopropionic Acid as the carboxylic acid component. $^1$H NMR: (CDCl$_3$, 200 MHz) (2 rotamers) δ7.80–6.80 (21 Ar—H), 5.40 (br s, 1H, CONH), 4.62, 4.51 (2 m, 1H, H5), 4.41–4.28 (m, 3H, CH$_2$CH), 4.20 (m, 1H, H3), 3.78 (s, 6H, OCH$_3$), 3.92, 3.65 (2 m, 2H, H2a), 3.70–3.30 (m, 4H, H2b, COCH$_2$CH$_2$NHCO, H6a), 3.15 (m, 1H, H6b), 2.60–1.90 (3m, 4H, H4a,b, COCH$_2$CH$_2$NHCO).

EXAMPLE 14

N-Imidazolyl-2-Acetic acid.

Imidazole (3.7 g, 54 mmol) was added to a suspension of sodium hydride (2.6 g of a 60% dispersion in oil, 60 mmol) in 50 ml dry THF. Bromoacetic acid (3.4 g, 24 mmol) was then added and the mixture stirred overnight. Water (1 ml) was then added and the solvent removed under reduced pressure. The residue was taken up in water (50 ml, pH>10), extracted with ether and the organic layer discarded. The aqueous layer was acidified to pH 1 with concentrated HCl and extracted again with ether. The aqueous layer was evaporated to dryness. The oily residue was dissolved in absolute ethanol (EtOH) to precipitate NaCl, and recrystallized from acetone/methanol to give 1.22 g (7.5 mmol, 30%) pure product as the hydrochloride. $^1$H NMR: (DMSO-d6, 200 MHz) δ9.20 (s, H2), 7.76 (d, J=1.5 Hz), 7.69 (d, J=1.5 Hz), 5.20 (s, CH$_2$). 0

EXAMPLE 15

$N^1$-(N-imidazolyl-2-Acetyl)-5-Dimethoxytrityloxymethyl-3-Hydroxypyrrolidine

This compound was prepared as per the procedure described in Example 5 using N-imidazolyl-2-acetic acid as the carboxylic acid component. $^1$H NMR: (DMSO-d6, 200 MHz) (2 rotamers) δ7.50–6,80 (3 imidazole-H, 13 Ar—H), 4.90 (ABq, 2H, COCH$_2$), 4.44 (m, 1H, H5), 4.28, 4.15 (m, 1H, H3), 3.70 (s, 6H, OCH$_3$), 3.66 (m, 1H, H2a), 3.39 (m, 1H, H2b), 3.35–3.00 (m, 2H, H6a, H6b), 2.08–1.82 (m, 2H, H4a, H4b).

EXAMPLE 16

(9-Adenine)-2-Acetic Acid Ethyl Ester.

Sodium hydride (8.20 g 60% in oil, 205 mmol) was added to a suspension of adenine (25.0 g, 185 mmol) in 500 ml DMF. After 2 hour vigorous mechanical stirring H$_2$ evolution stopped and a thick slurry was obtained. Ethyl bromoacetate (55.6 g, 36.9 ml, 333 mmol) was added dropwise over 3 hours, and stirring continued for a further 1 hour. Water (10 ml) and H$_2$SO$_4$ were added to pH 4. The solvent was evaporated and the residue suspended in 500 ml H$_2$O, filtered and washed with water. The residue was recrystallized from 400 ml ethanol to give 23.8 g (108 mmol, 58%) pure product.

EXAMPLE 17

(N2-Benzoyl-9-Adenine)-2-Acetic Acid.

To a suspension of (9-adenylyl)-2-acetic acid ethyl ester (6.06 g, 27.4 mmol) in 250 ml dry pyridine was added benzoyl chloride (9.60 ml, 11.6 g, 82 mmol), and the solution stirred for 4 hours at room temperature. Methanol (25 ml) was added and the solvents evaporated. The residue was dissolved in ethyl acetate (2×250 ml), washed with 0.1N HCl, H$_2$O, saturated NaHCO$_3$, brine, and dried with Na₂SO₄. The organic extracts were evaporated and the solid residue was redissolved in 250 ml THF at 0° C., to which was added 100 ml 1M NaOH. The solution was stirred at 0° C. for 1 hour and acidified to pH 1 with concentrated HCl, and the aqueous portion extracted once with ether. The product, which began to crystallize almost immediately, was collected by filtration to yield 4.96 g (61%). $^1$H NMR: (DMSO-d6, 200 MHz) δ8.86, 8.84 (d, H2, H8), 8.1 (d, 2H, J=7.0 Hz, ArH), 7.69–7.58 (m, 3H, Ar—H), 5.22 (s, 2H, CH₂).

EXAMPLE 18

$N^1$-[(N2-Benzoyl-9-Adenine)-2-Acetyl]-5-Dimethoxytrityloxymethyl-3-Hydroxypyrrolidine.

This compound was prepared as per the procedure described in Example 5 using (N2-benzoyl-9-adenine)-2-acetic acid as the carboxylic acid component. $^1$H NMR: (DMSO-d6, 200 MHz) (2 rotamers) δ8.67, 8.34 (2 s, 2H, adenine H2, H8) 8.04 (d, 2H, benzoyl H2, H6), 7.54 (m, 3H, benzoyl H3,4,5), 7.35–7.10, 6.84 (13 Ar—H), 5.22 (ABq, 2H, COCH₂), 4.50, 4.34 (2 m, 1H, H5), 4.23, 4.15 (2 m, 1H, H3), 4.05, 3.80 (m, 1H, H2a), 3.70 (s, 6H, OCH₃), 3.93, 3.55 (m, 1H, H2b), 3.35, 3.18 (m, 2H, H6a), 3.28, 2.98 (m, 1H, H6B), 2.30–1.84 (4 m, 2H, H4a, H4b).

EXAMPLE 19

N4-Benzoyl-1-Cytosine-2-Acetic Acid.

Cytosine hemihydrate (12.0 g, 100 mmol) was dried by coevaporation with pyridine, redissolved in dry pyridine (250 ml), and benzoyl chloride added dropwise (70.3 g, 500 mmol) with cooling. The solution was stirred overnight, water added and the solvent removed in vacuo. The residue was dissolved in 700 ml H₂O containing 55 g NaOH. Once complete dissolution had occurred stirring was continued for one hour. The solution was then acidified to pH 4, and the white precipitate collected, boiled in 1 L ethanol and filtered again to give 16.1 g benzoylcytosine. Fifteen grams of this was suspended in 500 ml DMF with 9.7 g (70 mmol) K₂CO₃ and methyl bromoacetate (10.7 g, 70 mmol). The suspension was stirred for 3 days, filtered and the solvent removed. Water was added (100 ml) and 10 ml 4N HCl. The suspension was stirred 15 minutes and filtered. The solid was resuspended in 200 ml H₂O containing 4.8 g NaOH. The suspension was stirred 45 minutes until all the solid had dissolved. The solution was then acidified to pH 2, the solid collected by filtration and dried to give 10.6 g product (43%). The product was identified by NMR.

EXAMPLE 20

$N^1$-[(N4-Benzoyl-1-Cytosine)-2-Acetyl]-5-Dimethoxytrityloxymethyl-3-Hydroxypyrrolidine.

The title compound is prepared via the procedure of Example 5 using N4-benzoyl-1-cytosine-2-acetic acid as the carboxylic acid component.

EXAMPLE 21

N2-Isobutyroyl-9-Guanine-2-Acetic Acid.

To a suspension of 2-amino-6-chloropurine (10 mmol) and K₂CO₃ (15 mmol) in DMF (25 ml) is added ethyl bromoacetate (10 mmol). The mixture is stirred vigorously for 24 hours, filtered and the solvent evaporated. The residue is resuspended in 25 ml pyridine and isobutyroyl chloride added (20 mmol). After stirring for 18 hours, water is added and the solvent removed. The residue is suspended in 1N HCl and heated to reflux for 1 hour. The suspension is then cooled to 0° C., NaOH added to pH 12, and the suspension stirred for 1 hour. The solution is acidified to pH 3, and the product is collected by filtration.

EXAMPLE 22

$N^1$-[(N2-Isobutyroyl-9-Guanine)-2-Acetyl]-5-Dimethoxytrityloxymethyl-3-Hydroxypyrrolidine.

The title compound is prepared via the procedure of Example 5 using N2-isobutyroyl-9-guanine-2-acetic acid as the carboxylic acid component.

EXAMPLE 23

Benzyl 3,6,9,12-Tetraoxatridecanoate.

Triethyleneglycol monomethyl ether (10 mmol) and benzyl bromoacetate (11 mmol) are added to a suspension of anhydrous K₂CO₃ (15 mmol) in 50 ml anhydrous DMF. The suspension is stirred at room temperature overnight. Water is added and the emulsion is extracted with ethyl acetate (3×200 ml), washed with water, brine, and dried with MgSO₄. The solvent is evaporated and the residual oil purified by flash chromatography to give the title compound.

EXAMPLE 24

3,6,9,12-Tetraoxatridecanoic Acid.

Benzyl-3,6,9,12-Tetraoxatridecanoate (5 mmol) is dissolved in methanol (50 ml) and 10% palladium on carbon is added (100 mg catalyst/mmol). The suspension is shaken under 30 psi H₂ until the starting material is consumed. The suspension is filtered through a short pad of Celite, washed thoroughly with methanol, and the solvent evaporated. The product is used directly without purification.

EXAMPLE 25

$N^1$-[3,6,9,12-Tetraoxatridecanoyl]-5-Dimethoxytrityloxymethyl-3-Hydroxypyrrolidine.

The title compound is prepared via the procedure of Example 5 using 3,6,9,12-tetraoxatridecanoic acid as the carboxylic acid component.

EXAMPLE 26

Benzyl Bis-[(2-pyridyl)-2-ethyl]-Aminoacetate.

To a suspension of K₂CO₃ (15 mmol) in 25 ml DMF was added 2,2'-bis(2-pyridylethyl)-amine (10 mmol) followed by benzyl bromoacetate (12 mmol). The suspension was stirred for 4 hour at room temperature. Water was then added, and the suspension extracted with ethyl acetate (2×100 ml), washed with 5% Na₂CO₃, water, brine, dried with MgSO₄ and the solvents removed. The product was obtained as an oil in quantitative yield. Product was identified by NMR.

EXAMPLE 27

Bis(2-(2-Pyridyl)ethyl)-Aminoacetic Acid.

Benzyl bis-[(2-pyridyl)-2-ethyl]-aminoacetate (5 mmol) is dissolved in methanol (50 ml) and 10% palladium on carbon is added (100 mg catalyst/mmol). The suspension is shaken under 30 psi H₂ until the starting material is consumed. The suspension is filtered through a short pad of Celite, washed thoroughly with methanol, and the solvent evaporated. The product is used directly without purification.

EXAMPLE 28

$N^1$-[Bis(2-(2-Pyridyl)ethyl)-Aminoacetyl]-5-Dimethoxytrityloxymethyl-3-Hydroxypyrrolidine.

This compound is prepared via the procedure of Example 5 using bis(2-(2-pyridyl)ethyl)-aminoacetic acid as the carboxylic acid component.

EXAMPLE 29

$N^1$-(Toluenesulfonyl)-5-Dimethoxytrityloxymethyl-3-Hydroxypyrrolidine.

Chlorotrimethylsilane (6.0 mmol) is added dropwise to a solution of 5-DMT-hydroxypyrrolidine (5.0 mmol) in 25 ml dry pyridine. After stirring one hour, toluenesulfonyl chloride (6.0 mmol) is added in portions, and stirring continued for two hours. The reaction is quenched with saturated aqueous $NaHCO_3$, and the mixture stirred until the silyl ethers were hydrolyzed. The solvent is removed in vacuo, and the residue partitioned between water and ethyl acetate. The organic layer is washed with $NaHCO_3$, water, brine and dried with $Na_2SO_4$. The solvent is removed and the resulting oil purified by flash chromatography, using a gradient of MeOH in $CHCl_3$.

EXAMPLE 30

$N^2$-(Trifluoromethanesulfonyl)-5-Dimethoxytrityloxymethyl-3-Hydroxypyrrolidine.

Chlorotrimethylsilane (6.0 mmol) is added dropwise to a solution of 5-DMT-hydroxypyrrolidine (5.0 mmol) and triethylamine (15 mmol) in 50 ml dry $CH_2Cl_2$. After 1 hour the solution is cooled to −78° C., and trifluoromethanesulfonic anhydride (5.5 mmol) is added dropwise. The cooling bath is removed and the mixture allowed to warm to room temperature. The crude product is dissolved in pyridine and $NaHCO_3$ solution is added to hydrolyze the TMS ether. The solvent is evaporated, the residue partitioned between ethyl acetate and water, washed with $NaHCO_3$, brine and dried with $MgSO_4$. The residue is purified by flash chromatography using a gradient of methanol in $CHCl_3$.

EXAMPLE 31

$N^1$-Benzyl-5-Dimethoxytrityloxymethyl-3-Hydroxypyrrolidine.

Chlorotrimethylsilane (6.0 mmol) is added dropwise to a solution of 5-DMT-hydroxypyrrolidine (5.0 mmol), imidazole (5 mmol) and triethylamine (15 mmol) in 25 ml dry DMF. After stirring one hour the solvent is removed in vacuo, and the residue redissolved in acetonitrile (25 ml) and triethylamine (10 mmol). Benzyl bromide (6.0 mmol) is added, and stirring continued overnight. The reaction is quenched with saturated aqueous $NaHCO_3$, and the mixture stirred until the silyl ethers were hydrolyzed. The solvent is removed in vacuo, and the residue partitioned between water and ethyl acetate. The organic layer is washed with $NaHCO_3$, water, brine and dried with $Na_2SO_4$. The solvent is removed and the resulting oil purified by flash chromatography, using a gradient of MeOH in $CHCl_3$.

EXAMPLE 32

$N^1$-(Aminocarbonyl)-5-Dimethoxytrityloxymethyl-3-Hydroxypyrrolidine

Chlorotrimethylsilane (6.0 mmol) is added dropwise to a solution of 5-DMT-hydroxypyrrolidine (5.0 mmol) and triethylamine (15 mmol) in 50 ml dry $CH_2Cl_2$. After one hour, dimethylaminopyridine (1 mmol) is added followed by trimethylsilyl isocyanate (5.5 mmol). The solution is stirred until the starting material is consumed. The solvent is removed in vacuo and the crude product redissolved in pyridine and $NaHCO_3$ solution to hydrolyze the TMS ethers. The solvent is evaporated, the residue partitioned between ethyl acetate and water, washed with $NaHCO_3$, brine and dried with $MgSO_4$. The residue is purified by flash chromatography using a gradient of methanol in $CHCl_3$.

EXAMPLE 33

$N^1$-(Methylaminothiocarbonyl)-5-Dimethoxytrityloxymethyl-3-Hydroxypyrrolidine

Chlorotrimethylsilane (6.0 mmol) is added dropwise to a solution of 5-DMT-hydroxypyrrolidine (5.0 mmol) and triethylamine (15 mmol) in 50 ml dry $CH_2Cl_2$. After one hour, dimethylaminopyridine (1 mmol) is added followed by methylisothiocyanate (5.5 mmol). The solution is stirred until the starting material is consumed. The solvent is removed in vacuo and the crude product redissolved in pyridine and $NaHCO_3$ solution to hydrolyze the TMS ethers. The solvent is evaporated, the residue partitioned between ethyl acetate and water, washed with $NaHCO_3$, brine and dried with $MgSO_4$. The residue is purified by flash chromatography using a gradient of methanol in $CHCl_3$.

EXAMPLE 34

$N^1$-(Benzyloxycarbonyl)-3-Hydroxypyrrolidine-5-Methanol.

To a solution of N-CBz-4-hydroxy-L-proline (38.1 mmol) in 250 ml THF was added borane-methyl sulfide (78 mmol) dropwise at room temperature. After the evolution of $H_2$ had ceased, the solution was heated to reflux with mechanical stirring. After 1 hour a white precipitate had formed. Methanol was carefully added, and the resulting solution refluxed for a further 15 minutes. The solution was cooled to room temperature, the solvents evaporated under reduced pressure, and the residual gum coevaporated with 2×100 ml MeOH. The product was obtained as a viscous oil in quantitative yield and identified by NMR.

EXAMPLE 35

$N^1$-(Benzyloxycarbonyl)-5-Dimethoxytrityloxymethyl-3-Hydroxypyrrolidine.

$N^1$-(Benzyloxycarbonyl)-3-hydroxypyrrolidine-5-methanol (35.3 mmol) was coevaporated with dry pyridine (2×50 ml), redissolved in 200 ml dry pyridine, and cooled in an ice bath. Dimethoxytrityl chloride (38 mmol) was added in portions over 15 minutes, and the solution stirred at room temperature overnight. Methanol was then added (10 ml), and the solvent removed under reduced pressure. The resulting gum was redissolved in toluene (100 ml), filtered to remove the pyridinium hydrochloride and taken to dryness again. The residue was chromatographed (0 to 1.5% MeOH/$CH_2Cl_2$) to give the product. The product was identified by NMR.

EXAMPLE 36

N-α-(FMOC)-glutamic acid γ-benzyl ester.

To a solution of γ-benzyl glutamate (10 mmol) in 50 ml dioxane and 50 ml water is added triethylamine (25 mmol), followed by a solution of fluorenylmethyl chloroformate (11 mmol) in 50 ml dioxane. The mixture is vigorously stirred until the starting material is consumed. The solution is acidified to pH 2 with concentrated HCl, extracted with ethyl acetate (2×250 ml), washed with brine, dried with $MgSO_4$ and evaporated. The product is used without purification.

EXAMPLE 37

N-α-(FMOC)-γ-benzyl-L-glutamic acid fluorenylmethyl ester.

N-α-(FMOC)-glutamic acid γ-benzyl ester (5 mmol), fluorenylmethanol (5.5 mmol) and dimethylaminopyridine (0.5 mmol) are dissolved in 50 ml $CH_2Cl_2$. Dimethylaminopropyl ethyl carbodiimide (EDC, 6.0 mmol) is added, and the solution stirred at room temperature. After complete consumption of the starting material the solution is diluted with $CH_2Cl_2$, washed with 1% HCl, water and brine, dried with $MgSO_4$ and evaporated. The residue is purified by flash chromatography using ethyl acetate and hexane as eluant.

EXAMPLE 38

N-α-(FMOC)-L-glutamic acid α-fluorenylmethyl ester.

N-α-(FMOC)-γ-benzyl-L-glutamic acid fluorenylmethyl ester (5 mmol) is dissolved in methanol (50 ml) and 10% Palladium on carbon is added (100 mg catalyst/mmol). The suspension is shaken under 30 psi $H_2$ until the starting material is consumed. The suspension is filtered through a short pad of Celite, washed thoroughly with methanol, and the solvent evaporated. The product is used directly without purification.

EXAMPLE 39

$N^1$-(N-α-Fmoc-α-Fluorenylmethyl-γ-glutamyl)-5-Dimethoxytrityloxymethyl-3-Hydroxypyrrolidine The title compound is prepared by the procedure of Example 5 using N-α-(FMOC)-L-glutamic acid α-fluorenylmethyl ester as the carboxylic acid component.

EXAMPLE 40

N-Carbazolyl-2-Acetic acid.

The title compound is prepared as per Example 14 using carbazole as the starting heterocycle.

EXAMPLE 41

$N^1$-(N-Carbazolyl-2-Acetyl)-5-Dimethoxytrityloxymethyl-3-Hydroxypyrrolidine

This compound was prepared as per the procedure described in Example 5 using N-carbazolyl-2-acetic acid as the carboxylic acid component.

EXAMPLE 42

N-Pyrrolyl-2-Acetic acid.

The title compound is prepared as per Example 14 using pyrrole as the starting heterocycle.

EXAMPLE 43

$N^1$-(N-Pyrrolyl-2-Acetyl)-5-Dimethoxytrityloxymethyl-3-Hydroxypyrrolidine

This compound was prepared as per the procedure described in Example 5 using N-pyrrolyl-2-acetic acid as the carboxylic acid component.

EXAMPLE 44

$N^1$-Palmitoyl-5-Dimethoxytrityloxymethylpyrrolidine-3-O-[ (N,N-Diisopropylamino)-2-Cyanoethoxyphosphite]

To a solution of $N^1$-palmitoyl-5-dimethoxytrityloxymethyl-3-hydroxypyrrolidine in $CH_2Cl_2$ (0.1M) at 0° C. was added 3 equivalents of diisopropylethylamine, followed by 1.1 equivalents 2-cyanoethyl-N,N-diisopropylaminochlorophosphite. The solution was stirred at 0° C. until all the starting material was consumed. The solvent was removed in vacuo at low temperature and the resulting oil purified by flash chromatography using $EtOAc/CH_2Cl_2$ containing 1% triethylamine as eluant.

EXAMPLE 45

$N^1$- Phenylacetyl-5-Dimethoxytrityloxymethylpyrrolidine-3-O-[(N,N-Diisopropylamino)-2-Cyanoethoxyphosphite]

The title compound was prepared as per the procedure of Example 44 using $N^1$-phenylacetyl-5-dimethoxytrityloxymethyl-3-hydroxypyrrolidine of Example 7 as the starting material. $^{31}P$ NMR $CDCl_3 \delta$148.68, 148.26 and 147.72 (two rotamers).

EXAMPLE 46

$N^1$-(Fluorenylmethylsuccinoyl)-Dimethoxytrityloxymethylpyrrolidine- 3-O-[(N,N-Diisopropylamino)-2-Cyanoethoxyphosphite]

The title compound was prepared as per the procedure of Example 44 using $N^1$-(fluorenylmethylsuccinoyl)-5-dimethoxytrityloxymethyl-3-hydroxypyrrolidine of Example 9 as the starting material.

EXAMPLE 47

$N^1$-[(N-1-Thymidine)-2-acetyl]-5-Dimethoxytrityloxymethyl-3$N^1$-Dimethoxytrityloxymethylpyrrolidine-3-O-[(N,N-Diisopropylamino)-2-Cyanoethoxyphosphite]

The title compound was prepared as per the procedure of Example 44 using $N^1$-[(N-1-thymidine)-2-acetyl]-5-dimethoxytrityloxymethyl-3-hydroxypyrrolidine of Example 11 as the starting material.

EXAMPLE 48

$N^1$-(N-Fmoc-3-Aminopropionoyl)-Dimethoxytrityloxymethylpyrrolidine-3-O-[(N,N-Diisopropylamino)- 2-Cyanoethoxyphosphite]

The title compound was prepared as per the procedure of Example 44 using $N^1$-(N-Fmoc-3-Aminopropionoyl)-5-dimethoxytrityloxymethyl-3-hydroxypyrrolidine of Example 13 as the starting material. $^{31}P$ NMR $CDCl_3 \delta$148.82, 148.61 and 148.07 (two rotamers).

EXAMPLE 49

$N^1$-((N-Imidazolyl-2-Acetyl))-Dimethoxytrityloxymethylpyrrolidine-3-O-[(N,N-Diisopropylamino)-2-Cyanoethoxyphosphite]

The title compound was prepared as per the procedure of Example 44 using $N^1$-(N-imidazolyl-2-acetyl)-5-dimethoxytrityloxymethyl-3-hydroxypyrrolidine of Example 15 as the starting material. $^{31}P$ NMR $CDCl_3 \delta$149.2, 148.8, 148.1 and 147.4 (two rotamers).

EXAMPLE 50

$N^1$-(Isobutyroyl)-Dimethoxytrityloxymethylpyrrolidine-3-O-[(N,N-Diisopropylamino)-2-Cyanoethoxyphosphite]

The title compound was prepared as per the procedure of Example 44 using $N^1$-(isobutyroyl)-5-dimethoxytrityloxymethyl-3-hydroxypyrrolidine of Example 6 as the starting material. $^{31}P$ NMR $CDCl_3 \delta$148.6, 148.0, 147.8 and 146.8 (two rotamers).

EXAMPLE 51

$N^1$-[(N2-Benzoyl-9-Adenine)-2-Acetyl]-Dimethoxytrityloxymethylpyrrolidine-3-O-[(N,N-Diisopropylamino)-2-Cyanoethoxyphosphite]

The title compound was prepared as per the procedure of Example 44 using $N^1$-[(N2-benzoyl-9-adenine)-2-acetyl]-5-dimethoxytrityloxymethyl-3-hydroxypyrrolidine of Example 18 as the starting material.

EXAMPLE 52

$N^1$-[(N4-Benzoyl-1-Cytosine)-2-Acetyl]-Dimethoxytrityloxymethylpyrrolidine-3 -O-[(N,N-Diisopropylamino)-2-Cyanoethoxyphosphite]

The title compound was prepared as per the procedure of Example 44 using $N^1$-[(N4-benzoyl-1-cytosine)-2-acetyl]-5-dimethoxytrityloxymethyl-3-hydroxypyrrolidine of Example 20 as the starting material.

EXAMPLE 53

$N^1$-[(N2-Isobutyroyl-9-Guanylyl)-2-Acetyl]-Dimethoxytrityloxymethylpyrrolidine-3 -O-[(N,N-Diisopropylamino)-2-Cyanoethoxyphosphite]

The title compound was prepared as per the procedure of Example 44 using $N^1$-[(N2-isobutyroyl-9-guanylyl)-2-acetyl] -5-dimethoxytrityloxymethyl-3-hydroxypyrrolidine of Example as the starting material.

EXAMPLE 54

$N^1$-(3,6,9,12-Tetraoxatridecanoyl)-5-Dimethoxytrityloxymethylpyrrolidine-3 -O-[(N,N-Diisopropylamino)-2-Cyanoethoxyphosphite]

The title compound was prepared as per the procedure of Example 44 using $N^1$-(3,6,9,12-tetraoxatridecanoyl)-5-dimethoxytrityloxymethyl-3-hydroxypyrrolidine of Example 25 as the starting material.

EXAMPLE 55

$N^1$-{Bis[2-(2-Pyridyl)ethyl]-Aminoacetyl}-Dimethoxytrityloxymethylpyrrolidine-3 -O-[(N,N-Diisopropylamino)-2-Cyanoethoxyphosphite]

The title compound was prepared as per the procedure of Example 44 using $N^1$-{bis[2-(2-pyridyl)ethyl]-aminoacetyl}-5-dimethoxytrityloxymethyl-3-hydroxypyrrolidine of Example 28 as the starting material.

EXAMPLE 56

$N^1$-(Trifluoromethanesulfonyl)-5-Dimethoxytrityloxymethylpyrrolidine-3 -O-[(N,N-Diisopropylamino)-2-Cyanoethoxyphosphite]

The title compound was prepared as per the procedure of Example 44 using $N^1$-(trifluoromethanesulfonyl)-5-dimethoxytrityloxymethyl-3-hydroxypyrrolidine of Example 30 as the starting material.

EXAMPLE 57

$N^1$-(Benzyl)-5-Dimethoxytrityloxymethylpyrrolidine-3-O-[(N,N-Diisopropylamino)-2-Cyanoethoxyphosphite]

The title compound was prepared as per the procedure of Example 44 using $N^1$-(benzyl)-5-dimethoxytrityloxymethyl-3-hydroxypyrrolidine of Example 31 as the starting material.

EXAMPLE 58

$N^1$-(Aminocarbonyl)-5-Dimethoxytrityloxymethylpyrrolidine-3-O-[(N,N-Diisopropylamino)-2-Cyanoethoxyphosphite]

The title compound was prepared as per the procedure of Example 44 using $N^1$-(aminocarbonyl)-5-dimethoxytrityloxymethyl-3-hydroxypyrrolidine of Example 32 as the starting material.

EXAMPLE 59

$N^1$-(Methylaminothiocarbonyl)-2-Acetyl]-Dimethoxytrityloxymethylpyrrolidine-3 -O-[(N,N-Diisopropylamino)-2-Cyanoethoxyphosphite]

The title compound was prepared as per the procedure of Example 44 using $N^1$-(methylaminothiocarbonyl)-2-acetyl] -5-dimethoxytrityloxymethyl-3-hydroxypyrrolidine of Example 33 as the starting material.

EXAMPLE 60

$N^1$-(Benzyloxycarbonyl)-5-Dimethoxytrityloxymethylpyrrolidine-3 -O-[(N,N-Diisopropylamino)-2-Cyanoethoxyphosphite]

The title compound was prepared as per the procedure of Example 44 using $N^1$-(benzyloxycarbonyl)-5-dimethoxytrityloxymethyl-3-hydroxypyrrolidine of Example 35 as the starting material.

EXAMPLE 61

$N^1$-(N-α-Fmoc-α-Fluorenylmethyl-γ-glutamyl)-5-Dimethoxytrityloxymethylpyrrolidine-3 -O-[(N,N-Diisopropylamino)-2-Cyanoethoxyphosphite]

The title compound was prepared as per the procedure of Example 44 using $N^1$-(N-α-Fmoc-α-fluorenylmethyl-γ-glutamyl)-5-dimethoxytrityloxymethyl-3-hydroxypyrrolidine of Example 39 as the starting material.

EXAMPLE 62

Standard Oligomer Coupling Cycle Using Standard DNA Synthesis Protocols

The oligomeric macromolecules of the invention are synthesized on an automated DNA synthesizer (Applied Bio-systems model 380B) as is done with standard oligonucleotides using standard phosphoramidate chemistry with oxidation by iodine (see, Oligonucleotide Synthesis, A Practical Approach, M. J. Gait., ed., Oxford University Press, New York, 1990). For phosphorothioate oligomers, the standard oxidation bottle is replaced by 0.2M solution of 3H-1,2-benzodithiole-3-one 1,1-dioxide in acetonitrile for the step wise thiation of the phosphite linkages. The thiation wait step is increased to 68 sec and is followed by the capping step. After cleavage from the CPG column and deblocking in concentrated ammonium hydroxide at 55° C. (18 hours), the oligomers are purified by precipitation twice out of 0.5M NaCl solution with 2.5 volumes ethanol. Analytical gel electrophoresis is effected in 20% acrylamide, 8M urea, 454 mM Tris-borate buffer, pH=7.0. Phosphodiester and phosphorothioate oligomers are judged from polyacrylamide gel electrophoresis as to material length.

EXAMPLE 63

Synthesis of Sequence Specific Pyrrolidine Oligomer Having Phosphodiester Linkages "Aforvirsen" is an anti-papilloma agent having the nucleobase sequence:

TTG CTT CCA TCT TCC TCG TC.

A pyrrolidine phosphodiester linked oligomer of this preselected sequence is prepared using the T, A, C and G reagents from Examples 47, 51, 52 and 53, respectively, as per the procedure of Example 62 using iodine as the oxidation reagent to give the phosphodiester linked oligomeric compound having the "Aforvirsen" sequence.

EXAMPLE 64

Synthesis of Sequence Specific Pyrrolidine Oligomer Having Phosphorothioate Linkages A pyrrolidine phosphorothioate-linked oligomer of sequence TTG CTT CCA TCT TCC TCG TC is prepared using the T, A, C and G reagents from Examples 47, 51, 52 and 53, respectively, as per the procedure of Example 62 using 3H-1,2-benzodithiole-3-one 1,1-dioxide as the oxidation reagent to give the phosphorothioate linked oligomeric compound.

EXAMPLE 65

Incorporation Of Monomeric Units Into Oligomeric Structure Using Combinatorial Technique—General Procedure A solid support (universal support from Cambridge Research Biochemicals) is separated into portions of equal weight. The number of portions equals the number of monomers in the combinatorial library. Each portion is reacted with a desired amidites using tetrazole as catalyst, followed by oxidation of the phosphite triester to the phosphate as per the standard coupling cycle of Example 64 above. The DMT ether is cleaved using trichloroacetic acid in $CH_2Cl_2$ to regenerate the hydroxyl group at the end of the extended oligomer. The extent of the coupling reaction is optimized to be $\geq 90\%$ completed by varying the amidite concentration and total equivalents and the coupling time. After a coupling, the support is mixed thoroughly, then divided equally and amidites are again reacted individually to a portion of the support. This cycle is repeated for each random position until the 'fixed' position is reached.

At the 'fixed' position of the oligomer, each amidite is reacted individually to a portion of the support, but the portions are not mixed. Instead, each subset is further divided into the number of portions corresponding to the number of monomers. Each portion of support is then reacted with a different amidite, followed by mixing as above. Repeating this cycle for each of the different subsets of supports results in randomization in positions following the fixed position in the sequence. The resulting subsets are unique only in the fixed position.

At completion of the oligomer synthesis, the oligomers are cleaved from the solid support and phosphate protecting groups are removed by incubation for 1–2 hours at room temperature in concentrated ammonia. Supernatant containing the oligomer is then removed from the silica and incubated at 55° C. for 6–16 hours to cleave the protecting groups from the residues. The oligomer is desalted and protecting groups are removed by HPLC size exclusion chromatography.

EXAMPLE 66

Evaluation Of Coupling Efficiency Of Phosphoramidite Monomers

The following method is used to evaluate the hydroxyprolinol phosphoramidites or other phosphoramidites for suitability of use in a random sequence solid state oligomer synthesis. A solid-phase synthesis support containing an internal reference is used to determine coupling efficiency, estimate the extinction coefficient, and evaluate coupling-product quality of the test phosphoramidite monomers as follows:

A test monomer-support is selected as is an internal standard. Using dT as a symbol of thymidine, dC as a symbol for deoxy cytidine and other abbreviations as note in the text below, in an illustrative test system, thymidine bound to CPG, identified as dT-CPG, is used for the test monomer-support and 5'-O-acetyl capped cytosine bound to CPG, identified as 5'-Ac-dC-CPG, is used for the internal standard.

Reactive dT-CPG is mixed with a lesser molar equivalent of unreactive 5'-Ac-dC-CPG. The unreactive 5'-Ac-dC-CPG internal standard allows for accurate determination of unreacted dT present before and after a coupling reaction.

The peak area of dT can be identified as $A_T$ and the peak area of dC identified as $A_C$. The initial ratio of peak areas for dT and dC, i.e., $(A_T/A_C)_0$, is determined by cleavage, deprotection, and HPLC analysis of an aliquot of the CPG mixture. Measurements are taken at a wavelength of 260 nm. Relative moles of dC can be identified as C, and relative moles of dT can be identified as T. These are calculated from peak areas, $A_C$ and $A_T$, respectively, using known extinction coefficients: $C=A_C/\epsilon_C$ and $T=A_T/\epsilon_T$. Thus the relative peak area or molar amount of dT initially present can always be calculated from the peak area of dC:

$$A_{T0}=(A_C)[(A_T/A_C)_0]$$

$$T_0=(C)[(T/C)_0]$$

also,

|   |   |   |
|---|---|---|
|   | (C) (T/C) | $= (A_C/\epsilon_C) [(A_T/\epsilon_T)/(A_C/\epsilon_C)]$ |
|   |   | $= (A_C/\epsilon_C) (A_T/A_C)) (\epsilon_C/\epsilon_T)$ |
| thus, |   |   |
|   | (C) [(T/C)$_0$] | $= (A_C/\epsilon_C)) [(A_T/A_C)_0] (\epsilon_C, \epsilon_T)$ |
|   |   | $= (A_C/\epsilon_T) [(A_T/A_C)_0]$ |

An amidite monomer of interest, identified as X, is reacted with an aliquot of the CPG mixture. Reacted CPG is cleaved and deprotected with ammonia, then analyzed by HPLC to determine the area under the peak for dC, i.e., $A_C$; area under the peak for unreacted dT, i.e., $A_{T_{ur}}$; and area under the peak for X-T dimer, i.e., $A_{XT}$. These values are used to calculate coupling efficiency, C.E.; and X-T dimer extinction coefficient $\epsilon_{XT}$.

The coupling efficiency, C.E., is defined by the ratio of reacted dT, i.e., $T_r$, to total dT, i.e., $T_0$. Thus C.E.$=T_r/T_0$. Coupling efficiency can be determined from the relative moles of unreacted dT present before, i.e., $T_0$, and after, i.e., $T_{ur}$, coupling with X; all three are related by the equation $$T_0=T_r+T_{ur}$$

Since C.E. is a unit-less value, HPLC peak areas can be used instead of relative molar quantities to perform the calculation:

| | |
|---|---|
| C.E. | $= (T_r/T_0)$ |
| | $= (T_0/T_0) - (T_{ur}/T_0)$ |
| | $= 1 - (T_{ur}/T_0)$ |
| | $= 1 - (A_{Tur}/\epsilon_T)/(A_{T0}/\epsilon_T)$ |
| | $= 1 - (A_{Tur}/A_{T0})$ |
| | $= 1 - (A_{Tur}/[(A_C) [(A_T/A_C)_0]]$ |

The foregoing are all measurable quantities.

The extinction coefficient $\epsilon$ for X, i.e., in the given HPLC solvent system is determined from the C.E. for X and the relative areas of the HPLC peaks. The amount of X-T is equal to the amount of T that has reacted. $\epsilon$ for dimer X-T is defined as the peak area $A_{XT}$ divided by the moles of X-T dimer present XT, and is calculated as follows:

| | |
|---|---|
| XT | $= T_r$ |
| | $= (C.E.) (T_0)$ |
| $\epsilon_{XT}$ | $= (A_{XT}/XT)$ |
| | $= (A_{XT})/(C.E.) (T_0)$ |
| | $= (A_{XT})/(C.E.) (C) [(T/C)_0]$ |
| | $= (A_{XT})/(C.E.) (A_C/\epsilon_T) [(A_T/A_C)_0]$ |

These, again, are all measurable quantities.

Finally, the quality of the coupling-product X-T can be evaluated from the appearance of the HPLC chromatogram. Significant peaks (those summing >10% of product-peak area) other than those expected might also be addressed. Often they are the desired X-T dimer that retains protective groups. Disappearance of these peaks with extended ammonia treatment will confirm that the monomer requires extended ammonia deprotection beyond the standard time. In other cases the extra peaks can be identified as undesirable side-products or in some case they cannot be identified. Generally, coupling efficiency of less than about 90%, a required ammonia deprotection time of greater than a few days, or the occurrence of side-products amounting to greater that 10% (by UV absorbance) can be selected as initial guidelines to judge the possibility of excluding an amidite from consideration for use in a particular set of amidites used in generating random oligomeric compounds.

EXAMPLE 67

Evaluation Of Coupling Efficiency Of Illustrative Pyrrolidine Phosphoramidite Monomer The phenylacetylhydroxyprolinol phosphoramidite of Example 45 was coupled to a dT-CPG solid-phase synthesis support forming dimers and trimers. Coupling was effected as per the general procedure of Example 62. Synthesis of the dimers and trimers was performed with an ABI 394 DNA synthesizer (Applied Biosystems, Foster City, Calif.) using standard DNA synthesis reagents and synthesis protocols, with the exception of an extended (5 minute) coupling time added to the synthesis cycle. The oligomers were cleaved from solid support by treatment with concentrated ammonia for 3 days at 4° C. The supernatant was removed from the support and heated in a sealed vial at 55° C. for eight hours. This solution was cooled, and most of the ammonia removed by evaporation. The oligomers were analyzed directly on reversed-phase HPLC column (Waters Nova-Pak Phenyl, cat. #10656; Millipore Corp., Milford, Mass.) using a gradient of 1% to 75% acetonitrile in 0.1M ammonium acetate, pH 7, over 50 minutes. The HPLC system was a Waters with a 991 detector, 625 LC pump, and 714 WISP auto-injector. Calculations were performed using data collected at a wavelength of 260 nm.

In an iteration of this procedure, a dimer of the benzylhydroxyprolinol coupled to dT was synthesized as described above with the terminal DMT group removed to give a free terminal hydroxyl. The resulting crude mixture was analyzed by HPLC. Identification of all but one of the HPLC chromatogram peaks was made. The coupling efficiency and extinction coefficient of the dimer was determined using the general procedure described in Example 66, above, as follows:

| | |
|---|---|
| C.E. | $= 1 - (A_{Tur})/(A_C) [(A_T/A_C)_0]$ |
| | $= 1 - (7.20)/(16.16) (5.57) = 0.92$ (92%) |
| $\epsilon_{XT}$ | $= (A_{XT})/(C.E.) (A_C/\epsilon_T) [(A_T/A_C)_0]$ |
| | $= (68.34)/(.92) (7.20/8.71) (5.57)$ |
| | $= 16.1 \, M^{-1}cm^{-1} \, (10^{-3})$ |

The quality of the product was thus within a preselected ≧90% limit. The unaccounted for "impurity" material, represented only about 5% of the total area of the product peaks.

EXAMPLE 68

PLA$_2$ Assay

The oligomer libraries are screened for inhibition of PLA$_2$ in an assay using *E. coli* labeled with $^3$H-oleic acid (see, Franson, et al., *J. Lipid Res.* 1974, 15, 380; and Davidson, et al., *J. Biol. Chem.* 1987, 262, 1698) as the substrate. Type II PLA$_2$ (originally isolated from synovial fluid), expressed in a baculovirus system and partially purified, serves as a source of the enzyme. A series of dilutions of each the oligomeric pools is done in water: 10 µl of each oligomer is incubated for 5 minutes at room temperature with a mixture of 10 µPLA$_2$, 20 µl 5×PLA$_2$ Buffer (500 mM Tris 7.0–7.5, 5 mM CaCl$_2$), and 50 µl water. Each of the oligomer samples is run in duplicate. At this point, 10 µl of $^3$H *E. coli* cells is added. This mixture is incubated at 37° C. for 15 minutes. The enzymatic reaction is stopped with the addition of 50 µl 2M HCL and 50 µl fatty-acid-free BSA (20 mg/ml PBS), vortexed for 5 seconds, and centrifuged at high speed for 5 minutes. A 165 µl portion of each supernate is then put into a scintillation vial containing 6 ml of scintillant (Scinti-Verse) and cpms are measured in a Beckman Liquid Scintillation Counter. As a control, a reaction without oligomer is run alongside the other reactions as well as a baseline reaction containing no oligo as well as no PLA$_2$ enzyme. CPMs are corrected for by subtracting the baseline from each reaction data point.

EXAMPLE 69

Verification Of Assay

The PLA$_2$ test system of Example 68 was verified using phosphorothioate oligonucleotides with one or more strings of guanosine nucleotides (at least 3 per string). Libraries of these oligonucleotides were deconvoluted using the SURFs screening strategy and were shown to have an inhibitory effect on the PLA$_2$ enzyme. Knowing that phosphorothioate oligonucleotides inhibit PLA$_2$ with some sequence specificity, an eight nucleotide phosphorothioate library consisting of the four natural bases was used to test the assay system for suitability as a SURF screen. This library had been synthesized for use in another system and all subsets were not still available (indicated by dashes in Table III, below). Using the SURF method, it was confirmed that a stretch of guanosines were necessary for inhibition of PLA$_2$ activity by the phosphorothioate oligonucleotide (Table III, below).

The assay was sensitive and accurate enough to discriminate between subsets of oligomers so that an inhibitory sequence could be selected. In each of the first three rounds of selection, the most active subset was readily determined. After 5 rounds, there was little difference in the activity of the subsets with at least 5 G's in a row, suggesting that the terminal positions are not critical for the inhibitory activity. The IC$_{50}$ of the "winner" improves (enzyme activity decreases) as more of the positions are fixed. As a test of the reproducibility of the assay, an eight nucleotide phosphorothioate oligonucleotide of a single sequence (TTGGGGTT) was assayed with each round of testing. This oligonucleotide acted as an internal control of the accuracy of the assay; the IC$_{50}$ was 8 μM in each assay.

TABLE III

Inhibition of PLA$_2$ Activity by Library

Subsets IC$_{50}$ (Mm)

| | X = A | X = G | X = C | X = T |
|---|---|---|---|---|
| Round 2 NNGNXNNN | >50 | 25 | >50 | >50 |
| Round 3 NNXNCNCNN | — | 10 | >50 | — |
| Round 4 NNGGGXNN | 9 | 4 | 6 | 18 |
| Round 5 | | | | |
| NAGGGGXN | 4 | 2 | 4 | 4 |
| NGGGGGXN | 2.5 | 2 | 3 | 3 |
| NCGGGGXN | 5 | 4 | 5 | 5 |
| NTGGGGXN | 19 | 5 | 17 | 15 |

EXAMPLE 70

Assay of Library of Pyrrolidine Oligomeric Compounds Against PLA$_2$

A library containing the novel prolinol monomers is tested in the PLA$_2$ assay for identification of inhibitors of type II PLA$_2$. Confirmation of the "winner" is made to confirm that the oligomer binds to enzyme rather than substrate and that the inhibition of any oligomer selected is specific for type II PLA$_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and oligomer. $^{14}$C-labeled arachidonic acid released as a result of PLA$_2$-catalyzed hydrolysis is separated from substrate by thin layer chromatography and the radioactive product is quantitated. The "winner" is compared to phosphatidyl ethanolamine, the preferred substrate of human type II PLA$_2$, to confirm its activity. PLA$_2$ from other sources (snake venom, pancreatic, bee venom) and phospholipase C, phospholipase D and lysophospholipase can be used to further confirm that the inhibition is specific for human type II PLA$_2$.

EXAMPLE 71

Hybridization probe for the detection of specific mRNA in biological sample

For the reliable, rapid, simultaneous quantification of multiple varieties of mRNA in a biological sample without the need to purify the mRNA from other cellular components, a mRNA of interest from a suitable biological sample, i.e., mRNA of a blood borne virus, a bacterial pathogen product in stool, urine and other like biological samples, is identified using standard microbiological techniques. An oligomeric compound of the invention complementary to the nucleic acid sequence of this mRNA is prepared as per the above examples. The oligomeric compound is immobilized on insoluble CPG solid support utilizing the procedure of Pon, R. T., Protocols for Oligonucleotides and Analogs, Agrawal, S., Ed., Humana Press, Totowa, N.J., 1993, p 465–496. Using the method of PCT application WO 93/15221, a known aliquot of the biological sample under investigation is incubated with the insoluble CPG support having the oligomer thereon for a time sufficient to hybridize the mRNA to oligomer and thus to link the mRNA via the oligomer to the solid support. This immobilizes mRNA present in the sample to the CPG support. Other nonimmobilized materials and components are then washed off the CPG with a wash media suitable for use with the biological sample. The mRNA on the support is labelled with ethidium bromide, biotin or a commercial radionucleotide and the amount of label immobilized on the CPG support is measured to indicate the amount of mRNA present in the biological sample.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

We claim:

1. A compound having structure I:

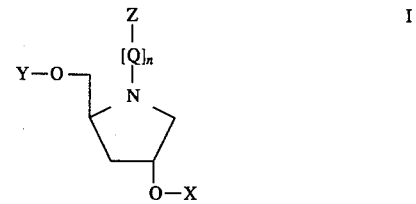

wherein:

X is H, a phosphate group, an activated phosphate group, an activated phosphite group, or a solid support;

Y is H or a hydroxyl protecting group;

Z is $L_{1a}$, $L_{1b}$–$G_1$, $L_2$, $L_2$–$G_2$, NR$_3$R$_4$, a nitrogen-containing heterocycle, a phosphate group, a polyether group, a polyethylene glycol group;

$L_{1a}$ is alkyl having 1 to about 20 carbon atoms, alkenyl having 2 to about 20 carbon atoms, or alkynyl having 2 to about 20 carbon atoms;

$L_{1b}$ is alkylene having 1 to about 20 carbon atoms, alkenylene having 2 to about 20 carbon atoms, or alkynylene having 2 to about 20 carbon atoms;

$L_2$ is aryl having 6 to about 14 carbon atoms or aralkyl having 7 to about 15 carbon atoms;

$G_1$ is halogen, OR$_1$, SR$_2$, NR$_3$R$_4$, C(=NH)NR$_3$R$_4$, NHC(=NH)NR$_3$R$_4$, CH=O, C(=O)OR$_5$, CH(NR$_3$R$_4$)(C(=O)OR$_5$), C(=O)NR$_3$R$_4$, a metal coordination group, or a phosphate group;

$G_2$ is halogen, OH, SH, SCH$_3$, or NR$_3$R$_4$;

R$_1$ is H, alkyl having 1 to about 6 carbon atoms, or a hydroxyl protecting group;

R$_2$ is H, alkyl having 1 to about 6 carbon atoms, or a thiol protecting group;

R$_3$ and R$_4$ are, independently, H, alkyl having 1 to about 6 carbon atoms, or an amine protecting group;

R$_5$ is H, alkyl having 1 to about 6 carbon atoms, or an acid protecting group;

Q is $L_{1b}$, $G_3$, $L_{1b}$–$G_3$ or $G_3$–$L_{1b}$–$G_3$;

$G_3$ is C(=O), C(=S), C(O)—O, C(O)—NH, C(S)—O, C(S)—NH or S(O)$_2$;

n is 0 or 1;

wherein if X is H, n is 1, and Q is $SO_2$, then Z is not aryl;

wherein if n is 0 and Z is $L_{1a}$, then X is not H; and wherein if n is 1 and Q is $L_{1b}$, then Z is not $L_{1a}$.

2. The compound of claim 1 wherein Y is a hydroxyl protecting group.

3. The compound of claim 2 wherein Y is trityl, methoxytrityl, dimethoxytrityl or trimethoxytrityl.

4. The compound of claim 1 wherein X is H, an activated phosphite group, or a solid support.

5. The compound of claim 4 wherein X is a phosphoramidite.

6. The compound of claim 1 wherein n is 1 and Q is carbonyl, carboxy, acetyl or succinyl.

7. The compound of claim 1 wherein Z is a nitrogen-containing heterocycle.

8. The compound of claim 7 wherein said heterocycle is imidazole, pyrrole, or carbazole.

9. The compound of claim 8 wherein Z is imidazole.

10. The compound of claim 1 wherein Z is a purine or a pyrimidine.

11. The compound of claim 10 wherein Z is adenine, guanine, cytosine, uridine, or thymine.

12. The compound of claim 11 wherein Q is acetyl.

13. The compound of claim 1 wherein Z is alkyl having 1 to about 20 carbon atoms.

14. A compound having structure I:

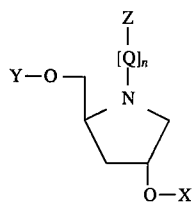

wherein:

X is H, a phosphate group, an activated phosphate group, an activated phosphite group, or a solid support;

Y is H or a hydroxyl protecting group;

Z is aryl having 6 to about 14 carbon atoms or aralkyl having 7 to about 15 carbon atoms;

$L_{1b}$ is alkylene having 1 to about 20 carbon atoms, alkenylene having 2 to about 20 carbon atoms, or alkynylene having 2 to about 20 carbon atoms;

Q is $L_{1b}$, $G_3$, $L_{1b}$–$G_3$ or $G_3$–$L_{1b}$–$G_3$;

$G_3$ is C(=O), C(=S), C(O)—O, C(O)—NH, C(S)—O, C(S)—NH or $S(O)_2$; and n is 0 or 1;

wherein if X is H, n is 1, and Q is $SO_2$, then Z is not aryl.

15. The compound of claim 14 wherein Z is fluorenylmethyl, phenyl, or benzyl.

16. A compound having structure I:

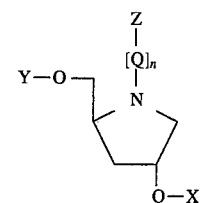

wherein:

X is H, a phosphate group, an activated phosphate group, an activated phosphite group, or a solid support;

Y is H or a hydroxyl protecting group;

Z is polyethylene glycol or glutamyl;

$L_{1b}$ is alkylene having 1 to about 20 carbon atoms, alkenylene having 2 to about 20 carbon atoms, or alkynylene having 2 to about 20 carbon atoms;

Q is $L_{1b}$, $G_3$, $L_{1b}$–$G_3$ or $G_3$–$L_{1b}$–$G_3$;

$G_3$ is C(=O), C(=S), C(O)—O, C(O)—NH, C(S)—O, C(S)—NH or $S(O)_2$;

n is 0 or 1.

* * * * *

UNITED STATES PATENT AND TRADEMARK OFFICE
CERTIFICATE OF CORRECTION

PATENT NO. : 5,519,134
DATED : May 21, 1996
INVENTOR(S) : Acevedo et al.

It is certified that error appears in the above-indentified patent and that said Letters Patent is hereby corrected as shown below:

Column 29, in Table III, line 22, remove "NNXNCNCNN" and insert --NN<u>G</u>X<u>G</u>NNN--.

Signed and Sealed this

Eighteenth Day of March, 1997

Attest:

BRUCE LEHMAN

Attesting Officer

Commissioner of Patents and Trademarks